US005919652A

United States Patent [19]

Pang et al.

[11] Patent Number: 5,919,652

[45] Date of Patent: Jul. 6, 1999

[54] NUCLEIC ACID MOLECULES COMPRISING THE PROSTATE SPECIFIC ANTIGEN (PSA) PROMOTER AND USES THEREOF

[75] Inventors: Shen Pang, Van Nuys; Arie S. Belldegrun, Los Angeles, both of Calif.

[73] Assignee: The Regents of the University of California, Oakland, Calif.

[21] Appl. No.: 08/522,841

[22] Filed: Sep. 1, 1995

Related U.S. Application Data

[63] Continuation-in-part of application No. 08/336,410, Nov. 9, 1994, abandoned.

[51] Int. Cl.[6] .......................... C12P 21/00; C12N 15/85; C12N 5/10; C07H 21/04

[52] U.S. Cl. .................... 435/69.1; 435/320.1; 435/325; 435/366; 536/24.1

[58] Field of Search ............................... 435/69.1, 172.1, 435/172.3, 240.2, 320.1, 325, 366; 536/23.1, 23.5, 24.1; 424/93.2, 93.6; 514/44

[56] References Cited

U.S. PATENT DOCUMENTS

| | | | |
|---|---|---|---|
| 5,087,572 | 2/1992 | Castellino et al. | 435/359 |
| 5,168,062 | 12/1992 | Stinski | 435/366 |
| 5,648,478 | 7/1997 | Henderson | 536/24.1 |

OTHER PUBLICATIONS

Orkin et al., "Report and Recommendations of the Panel to Assess the NIH Investment in Research on Gene Therapy", Dec. 1995.

Klobeck et al., "Genomic sequence of human prostate specific antigen (PSA)," *Nucleic Acids Research,* vol. 17, No. 10, (1989) p. 3981.

P.H. Riegman et al., "The Promoter of the Prostate–Specific Antigen Contains a Functional Androgen Responsive Element", *Mol. Endo.* (1991) vol. 5, No. 12, pp. 1921–1929 (Exhibit 1).

H. Brady et al., "Specific Ablation of Human Immunodeficiency Virus Tat–Expressing Cells by Conditionally Toxic Retroviruses", *Proc. Natl. Acad. Sci. USA* (1994) vol. 91, pp. 365–369 (Exhibit 2).

D. Chan et al., "Prostate–Specific Antigen as a Marker for Prostatic Cancer: a Monoclonal and a Polyclonal Immunoassay Compared", *Clin. Chem.* (1987) vol. 33, No. 10, pp. 1916–1920 (Exhibit 3).

P. Murtha et al., "Characterization of an Androgen Response Element in the 5' Promoter Region of the Gene", *Biochemistry* (1993) vol. 32, No. 25, pp. 6459–6464 (Exhibit 4).

Z. Ram et al., "In Situ Retroviral–mediated Gene Transfer for the Treatment of Brain Tumors", Cancer Research (1993) *Cancer Research,* vol. 53, pp. 83–88 (Exhibit 5).

C. Lee et al., "Two–Dimensional Characterization of Prostatic Acid Phosphatase, Prostatic Specific Antigen and Prostate Binding Protein in Expressed Prostatic Fluid", *The Prostate,* 9:135–146, (1986) (Exhibit 6).

H. Hoogenboom, "Targeting of Tumor Necrosis Factor to Tumor Cells: Secretion by Myeloma Cells of a Genetically Engineered Antibody–tumor Necrosis Factor Hybrid Molecule", Biochimica et *Biophysica Acta,* vol. 1096, (1991) pp. 345–354 (Exhibit 7).

C. Fong et al., "Regulation of Prostatic Carcinoma Cell Proliferation and Secretory Activity by Extracellular Matrix and Stromal Secretions", *The Prostate,* 21:121–131 (1992) pp. 121–131 (Exhibit 8).

M. Izawa, "cDNA Cloning of Androgen–Stimulated mRNAs in Rat Seminal Vesicles: Partial Characterization of Newly isolated cDNA Clones, pSv–1 and pSv–2", *Endocrinol. Japon.* 37 (2), (1990) pp. 223–232 (Exhibit 9).

L. Venkatesh, "Selective Induction of Toxicity to Human Cells Expressing Human Immunodeficiency Virus Type 1 Tat by a Conditionally Cytotoxic Adenovirus Vector", *Proc. Natl. Acad. Sci.,* vol. 87, pp. 8746–8750, (1990) (Exhibit 10).

R. Henttu et al. "Androgens Up–Regulate the Human Prostate–Specific Antigen Messenger Ribonucleic Acid (mRNA), but Down–Regulate the Prostatic Acid Phosphatase mRNA in the LNCaP Cell Line", *Endocrinology,* vol. 130, No. 2, (1992) pp. 766–771 (Exhibit 11).

N. Ghyselinck et al., "Structural Organization and Regulation of the Gene for the Androgen–Dependent Glutathione Peroxidase–Like Protein Specific to the Mouse Epididymis", *Molecular Endocrinology,* (1993), pp. 258–269 (Exhibit 12).

G. Watwon et al., "Progressive Induction of mRNA Synthesis for Androgen–responsive Genes in Mouse Kidney", *Molecular and Cellular Endocrinology,* 68 (1990), pp. 67–74 (Exhibit 13).

L. Celis et al., "Proteins Interacting with an Androgen–responsive Unit in the C3(1) Gene Intron", *Molecular and Cellular Endocrinology,* 94 (1993) pp. 165–172 (Exhibit 14).

P. Rennie, et al., "Characterization of Two Cis–Acting DNA Elements Involved in the Androgen Regulation of the Probasin Gene", *Molecular Endocrinology,* vol. 7, No. 1, (1993), pp. 23–36 (Exhibit 15).

T. Wang et al., "Preliminary Evaluation of Measurement of Serum Prostate–Specific Antigen Level in Detection of Prostate Cancer", *Annals of Clinical and Laboratory Science,* vol. 16, No. 6, (1986), pp. 461–466 (Exhibit 16).

N. Dawson, "Treatment of Progressive Metastatic Prostate Cancer", *Oncology,* vol. 7, No. 5, (1993), pp. 17–24 (Exhibit 17).

S. Pang et al., "High Levels of Unintegrated HIV–1 DNA in Brain Tissue of AIDS Dementia Patients", *Nature,* vol. 343, (1990), pp. 85–89 (Exhibit 18).

(List continued on next page.)

*Primary Examiner*—David Guzo
*Attorney, Agent, or Firm*—Mandel & Adriano

[57] ABSTRACT

The present invention provides isolated or purified nucleic acid molecules comprising a prostate specific antigen (PSA) promoter alone or in combination with a cytomegalovirus (CMV) promoter.

13 Claims, 12 Drawing Sheets

OTHER PUBLICATIONS

S. Kuriyama et al., "A Potential Approach for Gene Therapy Targeting Hepatoma Using a Liver–Specific Promoter on a Retroviral Vector", *Cell Structure and Function,* vol. 16, (1991) pp. 503–509 (Exhibit 19).

C. Young et al., "Hormonal Regulation of Prostate–specific Antigen Messenger RNA in Human Prostatic Adenocarcinoma Cell Line LNCaP", *Cancer Research,* vol. 51, (1991) pp. 3748–3752 (Exhibit 20).

W. Tilley et al., "Androgen Receptor Gene Expression in Human Prostate Carcinoma Cell Lines", *Cancer Research,* vol. 50, (1990) pp. 5382–5386 (Exhibit 21).

C. Huggins et al., "I. The Effect of Castration, of Estrogen and of Androgen Injection on Serum Phosphatases in Metastatic Carcinoma of the Prostate", *Studies on Prostatic Cancer,* (1941), pp. 293–297 (Exhibit 22).

R. Vile et al., "In Vitro and in Vivo Targeting of Gene Expression to Melanoma Cells", *Cancer Research,* vol. 53, (1993), pp. 962–966 (Exhibit 23).

L. Emtage et al., "The Role of Prostate Specific Antigen in the Baseline Assessment of Patients Undergoing Hormone Therapy for Advanced Prostate Cancer", *British Journal of Urology,* (1987) 60:572–577 (Exhibit 24).

a.

b.

c.

d.

e.

1 GTCGACATTG ATTATTGACT AGTTATTAAT AGTAATCAAT TACGGGGTCA TTAGTTCATA
61 GCCCATATAT GGAGTTCCGC GTTACATAAC TTACGGTAAA TGGCCCGCCT GGCTGACCGC
121 CCAACGACCC CCGCCCATTG ACGTCAATAA TGACGTATGT TCCCATAGTA ACGCCAATAG
181 GGACTTTCCA TTGACGTCAA TGGGTGGACT ATTTACGGTA AACTGCCCAC TTGGCAGTAC
241 ATCAAGTGTA TCATATGCCA AGTACGCCCC CTATTGACGT CAATGACGGT AAATGGCCCG
301 CCTGGCATTA TGCCCAGTAC ATGACCTTAT GGGACTTTCC TACTTGGCAG TACATCTACG
361 TATTAGTCAT CGCTATTACC ATGGTGATGC GGTTTTGGCA GTACATCAAT GGGCGTGGAT
421 AGCGGTTTGA CTCACGGGGA TTTCCAAGTC TCCACCCCAT TGACGTCAAT GGGAGTTTGT
481 TTTGGCACCA AAATCAACGG GACTTTCCAA AATGTCGTAA CAACTCCGCC CCATTGACGC
541 AAATGGGCGG TAGGCGTGTA CGGTGGGAGG TCTATATAAG CAGAGCTCTC TGGCTAACTA
601 GAGAACCCAC TGCTTAACTG GCTTATCGAA ATTAATACGA CTCACTATAG GGAGACCGGA
661 AGCTGATCTT TTTATGATGA CAGTAGCAAT GTATCTGTGG AGCTGGATTC TGGGTTGGGA
721 GTGCAAGGAA AAGAATGTAC TAAATGCCAA GACATCTATT TCAGGAGCAT GAGGAATAAA
781 AGTTCTAGTT TCTGGTCTCA GAGTGGTGCA GGGATCAGGG AGTCTCACAA TCTCCTGAGT
841 GCTGGTGTCT TAGGGCACAC TGGGTCTTGG AGTGCAAAGG ATCTAGGCAC GTGAGGCTTT
901 GTATGAAGAA TCGGGGATCG TACCCACCCC CTGTTTCTGT TTCATCCTGG GCATGTCTCC
961 TCTGCCTTTG TCCCCTAGAT GAAGTCTCCA TGAGCTACAA GGGCCTGGTG CATCCAGGGT
1021 GATCTAGTAA TTGCAGAACA GCAAGTGCTA GCTCTCCCTC CCCTTCCACA GCTCTGGGTG
1081 TGGGAGGGGG TTGTCCAGCC TCCAGCAGCA TGGGGAGGGC CTTGGTCAGC CTCTGGGTGC
1141 CAGCAGGGCA GGGGCGGAGT CCTGGGGAAT GAAGGTTTTA TAGGGCTCCT GGGGGAGGCT
1201 CCCCAGCCCC AAGCTT

```
  1 TTGGATTTTG AAATGCTAGG GAACTTTGGG AGACTCATAT TTCTGGGCTA GAGGATCTGT
 25 .......... .......... .......... .......... .......... ..........

 61 GGACCACAAG ATCTTTTTAT GATGACAGTA GCAATGTATC TGTGGAGCTG GATTCTGGGT
 85 .......... .......... .......... .......... .......... ..........

121 TGGGAGTGCA AGGAAAAGAA TGTACTAAAT GCCAAGACAT CTATTTCAGG AGCATGAGGA
145 .......... .......... .......... .......... .......... ..........

181 ATAAAAGTTC TAGTTTCTGG TCTCAGAGCG GTGCAGGGAT CAGGGAGTCT CACAATCTCC
205 .......... .......... ........T. .......... .......... ..........

241 TGAGTGCTGG TGTCTTAGGG CACACTGGGT CTTGGAGTGC AAAGGATCTA GGCACGTGAG
265 .......... .......... .......... .......... .......... ..........
  1         .. .........- ........-. .......... .......... ..........

301 GCTTTGTATG AAGAATCGGG GATCGTACCC ACCCCCTGTT TCTGTTTCAT CCTGGGCATG
325 .......... .......... .......... .......... .......... ..........
 51 .......... .......... .......... .......... .......... ..........

361 TCTCCTCTGC CTTTGTCCCC TAGATGAAGT CTCCATGAGC CACA-GGGCC TGGTGCATCC
385 .......... .......... .......... .......... T...A..... ..........
111 .......... .......... .......... .......... T...A..... ..........

420 AGGGTGATCT AGTAATTGCA GAACAGCAAG TACTAGCTCT CCCTCCCCTT CCACAGCTCT
445 .......... .......... .......... .G........ .......... ..........
171 .......... .......... .......... .G........ .......... ..........

480 GGGTGTGGGA GGGGGTTGTA CAGCCTCCAG CAGCATGGAG AGGGCCTTGG TCAGCCTCTG
505 .......... .........C .......... ........G. .......... ..........
231 .......... .........C .......... ........G. .......... ..........

540 GGTGCCAGCA GGGCAGGGGC GGAGTTCTGG GGAATGAAGG TTTTATAGGG CTCCTGGGGG
565 .......... .......... .....C.... .......... .......... ..........
291 .......... .......... .....C.... .......... .......... ..........

600 AGGCTCCCCA GCCCCAAGCT T  620
625 .......... .......... .  645
351 .......... .......... .  371
```

FIG. 11

```
   1 GTCGACATTG ATTATTGACT AGTTATTAAT AGTAATCAAT TACGGGGTCA TTAGTTCATA
  61 GCCCATATAT GGAGTTCCGC GTTACATAAC TTACGGTAAA TGGCCCGCCT GGCTGACCGC
 121 CCAACGACCC CCGCCCATTG ACGTCAATAA TGACGTATGT TCCCATAGTA ACGCCAATAG
 181 GGACTTTCCA TTGACGTCAA TGGGTGGACT ATTTACGGTA AACTGCCCAC TTGGCAGTAC
 241 ATCAAGTGTA TCATATGCCA AGTACGCCCC CTATTGACGT CAATGACGGT AAATGGCCCG
 301 CCTGGCATTA TGCCCAGTAC ATGACCTTAT GGGACTTTCC TACTTGGCAG TACATCTACG
 361 TATTAGTCAT CGCTATTACC ATGGTGATGC GGTTTTGGCA GTACATCAAT GGGCGTGGAT
 421 AGCGGTTTGA CTCACGGGGA TTTCCAAGTC TCCACCCCAT TGACGTCAAT GGGAGTTTGT
 481 TTTGGCACCA AAATCAACGG GACTTTCCAA AATGTCGTAA CAACTCCGCC CCATTGACGC
 541 AAATGGGCGG TAGGCGTGTA CGGTGGGAGG TCTATATAAG CAGAGCTCTC TGGCTAACTA
 601 GAGAACCCAC TGCTTAACTG GCTTATCGAA ATTAATACGA CTCACTATAG GGAGACCGGA
 661 AGCTGATCTT TTTATGATGA CAGTAGCAAT GTATCTGTGG AGCTGGATTC TGGGTTGGGA
 721 GTGCAAGGAA AAGAATGTAC TAAATGCCAA GACATCTATT TCAGGAGCAT GAGGAATAAA
 781 AGTTCTAGTT TCTGGTCTCA GAGCGGTGCA GGGATCAGGG AGTCTCACAA TCTCCTGAGT
 841 GCTGGTGTCT TAGGGCACAC TGGGTCTTGG AGTGCAAAGG ATCTAGGCAC GTGAGGCTTT
 901 GTATGAAGAA TCGGGGATCG TACCCACCCC CTGTTTCTGT TTCATCCTGG GCATGTCTCC
 961 TCTGCCTTTG TCCCCTAGAT GAAGTCTCCA TGAGCCACAG GGCCTGGTGC ATCCAGGGTG
1021 ATCTAGTAAT TGCAGAACAG CAAGTACTAG CTCTCCCTCC CCTTCCACAG CTCTGGGTGT
1081 GGGAGGGGGT TGTACAGCCT CCAGCAGCAT GGAGAGGGCC TTGGTCAGCC TCTGGGTGCC
1141 AGCAGGGCAG GGGCGGAGTT CTGGGGAATG AAGGTTTTAT AGGGCTCCTG GGGGAGGCTC
1201 CCCAGCCCCA AGCTT
```

NUCLEIC ACID MOLECULES COMPRISING THE PROSTATE SPECIFIC ANTIGEN (PSA) PROMOTER AND USES THEREOF

This application is a continuation-in-part of U.S. Ser. No. 08/336,410, filed Nov. 9, 1994, now abandoned, the contents of which is incorporated by reference into the present application.

Throughout this application various publications are referenced. The disclosures of these publications in their entireties are hereby incorporated by reference into this application in order to more fully describe the state of the art to which this invention pertains.

BACKGROUND OF THE INVENTION

Prostate cancer is the most commonly diagnosed neoplasm in men. The American Cancer Society estimates that 200,000 new cases of prostate cancer will be diagnosed in 1994, resulting in 38,000 deaths. The use of prostate-specific antigen (PSA), as a diagnostic agent, has been the most significant advance in prostate cancer diagnosis. PSA is an androgen-dependent serine protease produced by prostatic epithelial cells. Elevation of the serum PSA level is indicative of malignancy, yet it is important to realize that the test is not specific for cancer. PSA is also increased with benign prostatic hyperplasia, prostatitis, and trauma.

Present day therapeutic regimens for prostate cancer include radical prostatectomy, radiation therapy, androgen deprivation, and chemotherapy. In radical prostatectomy, the entire prostate, the seminal vesicles, the ampulla of the vas deferentia, and the overlying fascia are removed.

Radiation therapy includes both external and brachytherapy.

Radiation therapy is administered by exposing the patient to the beam of a linear accelerator or by implanting a radioisotope into the prostate gland.

Standard treatment for metastatic prostate cancer is androgen deprivation, achieved nonsurgically through interruption of testosterone production by the testis. Hormonal manipulation can be accomplished in a number of ways. The principal androgen for male reproductive function that affects prostate growth is testosterone. Luteinizing hormone-releasing hormone (LHRH) agonists are believed to inhibit LH release, which in turn inhibits testosterone levels, through a deregulation mechanism after an initial dramatic rise in LH production. LHRH agonists are often combined with nonsteroidal anti-androgens during the first 1 or 2 weeks of therapy to prevent this "flare" phenomenon with exacerbation of symptomatic disease. The expense of these agents limits their use.

Although use of nonsteroidal androgen antagonist is theoretically appealing, application is limited by the fact that androgen ablation does not impart a durable response and virtually all patients progress to an androgen refractory state with a median survival of twelve to eighteen months (C. Huggins and C. V. Hodges, *Cancer Res* 1,293 (1941)).

Further, testosterone and dihydrotestosterone bind intracellular receptors which limits its use in prostate cancer. Estrogens, such as diethylstilbestrol, can suppress LH production and inhibit androgen activity on a cellular level. These agents are quite effective in achieving androgen deprivation and are very inexpensive, but the potential of estrogens to increase the risk of thromboembolic cardiovascular disease in males has limited their use in recent years.

Chemotherapy has been of limited use in the management of disseminated disease. No effective agent has been identified as yet. Recently, investigators have evaluated the ability of suramin to inhibit the growth of prostate cancer. Response rates of 50% have been reported, although nearly all responses were partial. Duration of response is limited and toxicity is severe and common.

In the last few years, several new approaches for treating advanced neoplasms have been proposed, including that of gene therapy (S. U. Shin, *Biotherapy* 3, 43 (1991); H. R. Hoogenboom, U. C. Raus, G. Volckaert *Biochimica et Biophysica Acta* 1996, 345 (1991); S. Kunyama et al., *Cell Structure and Function* 16, 503 (1991); Z. Ram et al., *Cancer Research* 53, 83 (1993); R. G. Vile and I. R. Hart, *Cancer Research* 53, 962 (1993); J. A. Roth, *Seminars in Thoracic and Cardiovascular Surgery* 5, 178 (1993)).

The PSA gene sequence is known (Riegman P. H. J., Klaassen P., Korput J. A. G. M. van der, Romijn J. C., Trapman J. 1988 Molecular cloning and characterization of novel prostate antigen cDNAs. Biochem Biophys Res Commun 155:181–188; Riegman P. H. J., Vlietstra R. J., Korput J. A. G. M. van der, Romijn J. C., Trapman J. 1989 Characterization of the prostate-specific antigen gene: a novel kallikrein-like gene. Biochem Biophys Res Commun 159:95–102; Riegman P. H. J., Vlietstra R. J., Klaassen P., Korput J. A. G. M. van der, Romijn J. C., Trapman J. 1989 The prostate-specific antigen gene and the human glandular kallikrein-1 gene are tandemly located on chromosome 19. FEBS Lett 247:123–126; C. Lee et al., *Prostate* 9, 135 (1986); P. Schulz et al., *Nucleic Acids Research* 16, 6226 (1988); T. Y. Wang and T. P. Kawaguchi, *Annals of Clinical and Laboratory Science* 16, 461 (1988); D. W. Chan et al., *Clinical Chemistry* 33, 1916 (1987); L. A. Emtageet et al., *British Journal of Urology* 60, 572 (1987)).

The PSA promoter has been cloned by Riegman et al., (P. H. Riegman et al., *Molecular Endocrinology* 5, 1921 (1991)) and four protein binding subregions in this DNA fragment have been identified. An androgen-responsive element (ARE) was defined and has shown androgen responsiveness in COS cells, which are monkey kidney cells, cotransfected with the androgen receptor gene. To date, the tissue specificity of the PSA promoter has not been shown in prostate cells (P. H. Riegman, et al.)

Another study was done which utilized tissue-specific PSA promoter to drive a thymidine kinase (TK) gene that can convert the anti-viral agent acyclovir into a toxic metabolite. In this study, androgen-dependent (e.g., LNCaP), AI(C4, C4-2, DU-145, PC-3), and naive cells (e.g., WH and Hela cells) were infected with either a long PSA promoter (1600 bp) or short PSA promoter (630 bp) luciferase construct. The study showed that a long PSA promoter (1600 bp) at least 10-fold more potent than the short PSA promoter is better than short PSA promoter (630 bp) in inducing luciferase activity. Apparently, the long PSA promoter is better than the short PSA promoter in inducing luciferase activity. To date, the tissue specificity of the PSA promoter has not been characterized in prostate cells.

SUMMARY OF THE INVENTION

The present invention is a weapon that can be used as part of an arsenal of weapons against prostate cancer. It provides an isolated or purified nucleic acid molecule comprising a specific antigen (PSA) promoter.

The PSA promoter of the invention includes two embodiments. The first embodiment includes the PSA promoter as shown in FIG. 9 having a nucleic acid sequence beginning with guanine at nucleotide position 665 and ending with thymine at nucleotide position 1216 was cloned.

An alternative embodiment includes the PSA promoter designated as PC-PSA promoter as shown in FIG. 10 having a nucleic acid sequence beginning with guanine at nucleotide position 70 and ending with thymine at nucleotide position 620. The PC-PSA promoter was cloned and demonstrated a seven base pair difference to the Genbank sequences including the PSA promoter shown in FIG. 9.

In one embodiment of the invention, a heterologous gene sequence, i.e., a therapeutic gene, is inserted into the nucleic acid molecule of the invention. Other embodiments of the isolated nucleic acid molecule of the invention include the addition of a single enhancer element or multiple enhancer elements which amplify the expression of the heterologous therapeutic gene without compromising tissue specificity.

In one example, the enhancer element is at least a portion of the cytomegalovirus (CMV) promoter as shown in FIGS. 9 and 11. The sequence of the nucleic acid molecule comprising both the PSA and CMV promoters designated (1) the CMV-PSA promoter is shown in FIG. 9 and (2) the CMV-PC-PSA promoter is shown in FIG. 11

The present invention further relates to the use of recombinant DNA technology for in vivo gene transfer using the nucleic acid molecules of the invention. Specifically, the invention relates to the therapy of prostate cancer tumors using the nucleic acid molecules of the invention to make prostrate cancer cells sensitive to chemotherapeutic agents.

The promoter of the invention which directs expression of the therapeutic gene may be useful in constructing vectors for prostate cancer gene therapy.

BRIEF DESCRIPTION OF THE FIGURES

FIG. 9 is the nucleic acid sequence of the CMV-PSA promoter (SEQ ID NO: 3).

FIG. 10 is the nucleic acid sequence of the cloned PC-PSA promoter and its comparison to portions of known PSA promoter sequences (SEQ ID NOS: 4, 5 and 6).

FIG. 11 is the nucleic acid sequence of the CMV-PC-PSA promoter (SEQ ID NO: 7).

DETAILED DESCRIPTION OF THE INVENTION

Figure 1:
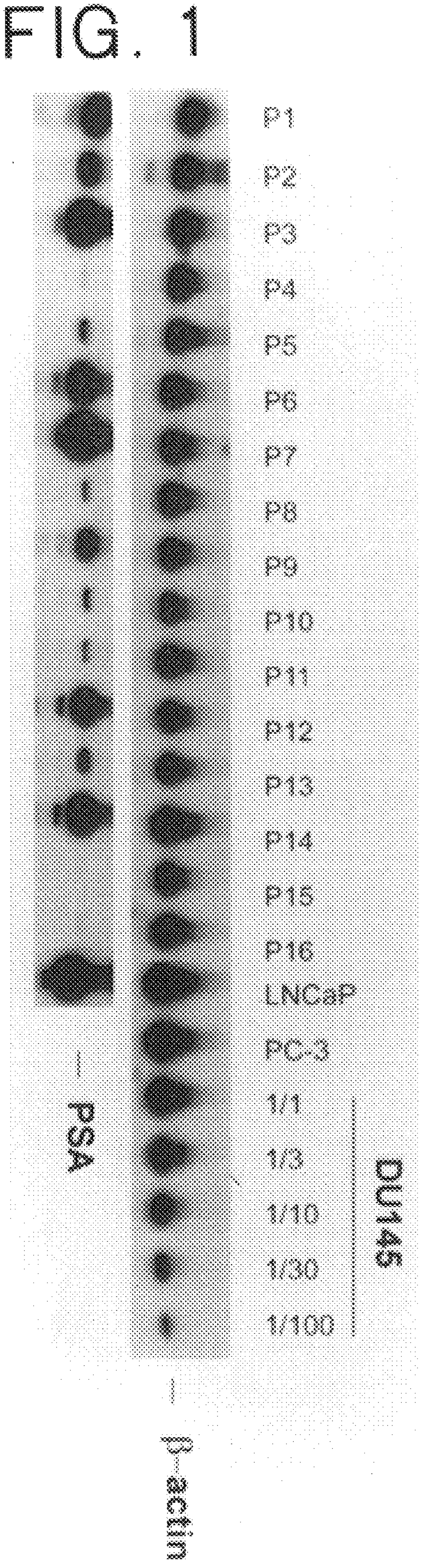
FIG. 1 is a gel showing RNA quantitation in patient tumor samples using a modified RT-PCR. RNA isolated from $10^4$ cells from LNCaP, PC-3 and DU145 cell lines was used as control for quantitation. Very high expression of PSA mRNA was detected in the samples from P1–3, P6–7, P9, P12 and P14. Lower, but significant expression was detected from P5, P8, P10–11 and P13.

In order that the invention herein described may be more fully understood, the following detailed description is set forth.

Definitions

As used herein "therapeutic gene" means DNA encoding an amino acid sequence corresponding to a functional protein capable of exerting a therapeutic effect on prostate cancer cells or having a regulatory effect on the expression of a function in prostate cells.

As used herein "nucleic acid molecule" includes both DNA and RNA and, unless otherwise specified, includes both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing.

As used herein "PSA promoter" means the PSA promoter having about 621-base pair (bp) fragment of DNA derived from the 5' flanking region of the prostate-specific antigen (PSA) gene as shown in FIG. 9 beginning with guanine at nucleotide position 665 and ending with thymine at nucleotide position 1216 or the PC-PSA promoter having the nucleic acid sequence beginning with guanine at nucleotide position 70 and ending with thymine at nucleotide position 620 as shown in FIG. 10.

As used herein "CMV-PSA promoter" is a cytomegalovirus IE1 promoter (CMV promoter) attached into the 5' flanking region of the PSA promoter.

As used herein "enhancer element" is a base sequence that increases the rate of transcription of the therapeutic genes or genes of interest but does not have promoter activity. An enhancer can be moved upstream, downstream, and to the other side of the PSA promoter without significant loss of activity.

Compositions of the Invention

The present invention provides an isolated nucleic acid molecule comprising a prostate specific antigen promoter, e.g., the PSA promoter as shown in FIG. 9 having a nucleic acid sequence beginning with guanine at nucleotide position 665 and ending with thymine at nucleotide position 1216 and the PC-PSA promoter as shown in FIG. 10 having a nucleic acid sequence beginning with guanine at nucleotide position 70 and ending with thymine at nucleotide position 620.

Preferably, the nucleic acid molecule further comprises a therapeutic gene.

In one embodiment, the isolated nucleic acid molecule of the invention, combines the PSA promoter with an enhancer element. In a preferred embodiment the enhancer element can be a portion of the CMV LTR or other enhancers, e.g. SV40 enhancer sequences, MMTV LTR. Other promoters are possible.

Preferably, the enhancer element, e.g., the CMV LTR, is positioned 5' of the PSA promoter in the molecule. In one embodiment of the invention, the nucleic acid molecule is shown in FIG. 10.

The nucleic acid molecule of the invention may be modified, i.e., by sequence mutations, deletions, and insertions, so as to produce derivative molecules. Other modifications include multiplying the number of sequences that can bind prostate cell specific regulatory proteins, deleting or tripling the number of GC Boxes or TATA Boxes in the CMV portion on the CMV-PSA promoter, deleting sequences that are nonfunctional in the PSA promoter. Modifications include adding other enhancers thereby improving the efficiency of the PSA promoters. Enhancers may function in a position-independent manner and can be within or downstream of the transcribed region.

Derivative molecules would retain the functional property of the PSA promoter, namely, the molecule having such substitutions will still permit the prostate tissue specific expression of the gene of interest. Modification is permitted so long as the derivative molecules retain its increased potency compared to PSA promoter alone and its tissue specificity.

In a preferred embodiment, a vector was constructed by inserting a heterologous sequence (therapeutic gene) into the nucleic acid molecule of the invention downstream of the modified PSA promoter.

Examples of therapeutic genes include suicide genes. These are genes sequences the expression of which produces a protein or agent that inhibits prostate tumor cell growth or prostate tumor cell death. Suicide genes include genes encoding enzymes, oncogenes, tumor suppressor genes, genes encoding toxins, genes encoding cytokines, or a gene encoding oncostatin. The purpose of the therapeutic gene is to inhibit the growth of or kill prostate cancer cell or produce cytokines or other cytotoxic agents which directly or indirectly inhibit the growth of or kill the prostate cancer cell.

Suitable enzymes include thymidine kinase (TK), xanthine-guanine phosphoribosyltransferase (GPT) gene from *E. coli* or *E. coli* cytosine deaminase (CD), or hypoxanthine phosphoribosyl transferase (HPRT).

Suitable oncogenes and tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), and nm23. Suitable toxins include Pseudomonas exotoxin A and S; diphtheria toxin (DT); *E. coli* LT toxins, Shiga toxin, Shiga-like toxins (SLT-1, -2), ricin, abrin, supporin, and gelonin.

Suitable cytokines include interferons, GM-CSF interleukins, tumor necrosis factor (TNF) (Wong G, et al., Human GM-CSF: Molecular cloning of the complementary DNA and purification of the natural and recombinant proteins. *Science* 1985; 228:810); WO9323034 (1993); Horisberger M. A., et al., Cloning and sequence analyses of cDNAs for interferon- and virus-induced human Mx proteins reveal that they contain putative guanine nucleotide-binding sites: functional study of the corresponding gene promoter. *Journal of Virology,* 1990 Mar, 64(3):1171–81; Li YP et al., Proinflammatory cytokines tumor necrosis factor-alpha and IL-6, but not IL-1, down-regulate the osteocalcin gene promoter. *Journal of Immunology,* Feb. 1, 1992, 148 (3):788–94; Pizarro T. T., et al. Induction of TNF alpha and TNF beta gene expression in rat cardiac transplants during allograft rejection. *Transplantation,* 1993 Aug., 56(2): 399–404). (Breviario F., et al., Interleukin-1-inducible genes in endothelial cells. Cloning of a new gene related to C-reactive protein and serum amyloid P component. *Journal of Biological Chemistry,* Nov. 5, 1992, 267(31):22190–7; Espinoza-Delgado I., et al., Regulation of IL-2 receptor subunit genes in human monocytes. Differential effects of IL-2 and IFN-gamma. *Journal of Immunology,* Nov. 1, 1992, 149(9):2961–8; Algate P. A., et al., Regulation of the interleukin-3 (IL-3) receptor by IL-3 in the fetal liver-derived FL5.12 cell line. *Blood,* 1994 May 1, 83(9) :2459–68; Cluitmans F. H., et al., IL-4 down-regulates IL-2-, IL-3-, and GM-CSF-induced cytokine gene expression in peripheral blood monocytes. *Annals of Hematology,* 1994 Jun., 68(6):293–8; Lagoo, A. S., et al., IL-2, IL-4, and IFN-gamma gene expression versus secretion in superantigen-activated T cells.

Distinct requirement for costimulatory signals through adhesion molecules. *Journal of Immunology,* Feb. 15, 1994, 152(4):1641–52; Martinez O. M., et al., IL-2 and IL-5 gene expression in response to alloantigen in liver allograft recipients and in vitro. *Transplantation,* 1993 May, 55(5): 1159–66; Pang G, et al., GM-CSF, IL-1 alpha, IL-1 beta, IL-6, IL-8, IL-10, ICAM-1 and VCAM-1 gene expression and cytokine production in human duodenal fibroblasts stimulated with lipopolysaccharide, IL-1 alpha and TNF-alpha. *Clinical and Experimental Immunology,* 1994 Jun., 96(3):437–43; Ulich T. R., et al., Endotoxin-induced cytokine gene expression in vivo. III. IL-6 mRNA and serum protein expression and the in vivo hematologic effects of IL-6. *Journal of Immunology,* Apr. 1, 1991, 146(7):2316–23; Mauviel A., et al., Leukoregulin, a T cell-derived cytokine, induces IL-8 gene expression and secretion in human skin fibroblasts. Demonstration and secretion in human skin fibroblasts. Demonstration of enhanced NF-kappa B binding and NF-kappa B-driven promoter activity. *Journal of Immunology,* Nov. 1, 1992, 149(9):2969–76).

Growth factors include Transforming Growth Factor-α (TGFα) and β(TGFβ), cytokine colony stimulating factors (Shimane M., et al., Molecular cloning and characterization of G-CSF induced gene cDNA. *Biochemical and Biophysical Research Communications,* Feb. 28, 1994, 199(1) :26–32; Kay A. B., et al., Messenger RNA expression of the cytokine gene cluster, interleukin 3 (IL-3), IL-4, IL-5, and granulocyte/macrophage colony-stimulating factor, in allergen-induced late-phase cutaneous reactions in atopic subjects. *Journal of Experimental Medicine,* Mar. 1, 1991, 173(3):775–8; de Wit H, et al., Differential regulation of M-CSF and IL-6 gene expression in monocytic cells. *British Journal of Haematology,* 1994 Feb., 86(2):259–64; Sprecher E., et al., Detection of IL-1 beta, TNF-alpha, and IL-6 gene transcription by the polymerase chain reaction in keratinocytes, Langerhans cells and peritoneal exudate cells during infection with herpes simplex virus-1. *Archives of Virology,* 1992, 126(1–4):253–69).

Preferred vectors for use in the methods of the present invention are viral including adenoviruses, retroviral, vectors, adeno-associated viral (AAV) vectors.

The viral vector selected should meet the following criteria: 1) the vector must be able to infect the tumor cells and thus viral vectors having an appropriate host range must be selected; 2) the transferred gene should be capable of persisting and being expressed in a cell for an extended period of time; and 3) the vector should be safe to the host and cause minimal cell transformation. Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other virus vectors that may be used for gene transfer into cells for correction of disorders include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses.

Adenoviruses have several properties that make them attractive as cloning vehicles (Bachettis et al.: Transfer of gene for thymidine kinase-deficient human cells by purified herpes simplex viral DNA. *PNAS USA,* 1977 74:1590; Berkner, K. L.: Development of adenovirus vectors for expression of heterologous genes. *Biotechniques,* 1988 6:616; Ghosh-Choudhury G., et al., Human adenovirus cloning vectors based on infectious bacterial plasmids. *Gene* 1986; 50:161; Hag-Ahmand Y., et al., Development of a helper-independent human adenovirus vector and its use in the transfer of the herpes simplex virus thymidine kinase gene. *J Virol* 1986; 57:257; Rosenfeld M., et al., Adenovirus-mediated transfer of a recombinant $\alpha_1$-antitrypsin gene to the lung epithelium in vivo. *Science* 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; identification of the component necessary for adenovirus translational control and their utilization in cDNA expression vectors. *PNAS USA,* 1985 82:689).

AAV is a small human parvovirus with a single stranded DNA genome of approximately 5 kb. This virus can be propagated as an integrated provirus in several human cell types. AAV vectors have several advantage for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduce genes can be rescued from the host cell by infection with a helper virus such as adenovirus.

HSV-1 vector system facilitates introduction of virtually any gene into non-mitotic cells (Geller et al. an efficient deletion mutant packaging system for a defective herpes simplex virus vectors: Potential applications to human gene therapy and neuronal physiology. *PNAS USA,* 1990 87:8950).

Another vector for mammalian gene transfer is the bovine papilloma virus-based vector (Sarver N, et al., Bovine papilloma virus DNA: A novel eukaryotic cloning vector. *Mol Cell Biol* 1981; 1:486).

Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA of infectious vaccine virus. *Proc Natl Acad Sci USA* 1982; 79:4927; Smith et al. infectious vaccinia virus recombinants that express hepatitis B virus surface antigens. *Nature,* 1983 302:490.)

Retroviruses are packages designed to insert viral genes into host cells (Guild B, et al., Development of retrovirus vectors useful for expressing genes in cultured murine embryonic cells and hematopoietic cells in vivo. *J Virol* 1988; 62:795; Hock R. A., et al., Retrovirus mediated transfer and expression of drug resistance genes in human hemopoietic progenitor cells. *Nature* 1986; 320:275).

The basic retrovirus consists of two identical strands of RNA packaged in a proviral protein. The core surrounded by a protective coat called the envelope, which is derived from the membrane of the previous host but modified with glycoproteins contributed by the virus.

Uses of the Compositions of the Invention

This invention involves targeting a gene-of-interest to the diseased prostate cancer site so that the protein encoded by the gene is expressed and directly or indirectly ameliorate the diseased state.

After infecting a susceptible cell, the transgene driven by a specific promoter in the vector expresses the protein encoded by the gene. The use of the highly specific prostate specific gene vector will allow selective expression of the specific genes in prostate cancer cells.

The present invention relates to a process for administering modified vectors into the prostate to treat prostate cancer or disorders associated with the prostate. More particularly, the invention relates to the use of vectors carrying functional therapeutic genes to produce molecules that are capable of directly or indirectly affecting cells in the prostate to repair damage sustained by the cells from defects, disease or trauma.

Preferably, for treating defects, disease or damage of cells in the prostate, vectors of the invention include a therapeutic gene or transgenes, for example a gene encoding TK. The genetically modified vectors are administered into the prostate to treat defects, disease such as prostate cancer by introducing a therapeutic gene product or products into the prostate that enhance the production of endogenous molecules that have ameliorative effects in vivo.

The basic tasks in the present method of the invention are isolating the gene of interest, selecting the proper vector vehicle to deliver the gene of interest to the body, administering the vector having the gene of interest into the body, and achieving appropriate expression of the gene of interest. The present invention provides packaging the cloned genes, i.e. the genes of interest, in such a way that they can be injected directly into the bloodstream or relevant organs of patients who need them. The packaging will protect the foreign DNA from elimination by the immune system and direct it to appropriate tissues or cells.

Along with the human or animal gene of interest another gene, e.g., a selectable marker, can be inserted that will allow easy identification of cells that have incorporated the modified retrovirus. The critical focus on the process of gene therapy is that the new gene must be expressed in target cells at an appropriate level with a satisfactory duration of expression.

The methods described below to modify vectors and administering such modified vectors into the prostate are merely for purposes of illustration and are typical of those that might be used. However, other procedures may also be employed, as is understood in the art.

Most of the techniques used to construct vectors and the like are widely practiced in the art, and most practitioners are familiar with the standard resource materials which describe specific conditions and procedures. However, for convenience, the following paragraphs may serve as a guideline.

General Methods for Vector Construction

Construction of suitable vectors containing the desired therapeutic gene coding and control sequences employs standard ligation and restriction techniques, which are well understood in the art (see Maniatis et al., in *Molecular Cloning:* A Laboratory Manual, Cold Spring Harbor Laboratory, New York (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog). In general, about 1 $\mu$g of plasmid or DNA sequences is cleaved by one unit of enzyme in about 20 $\mu$l of buffer solution. Typically, an excess of restriction enzyme is used to insure complete digestion of the DNA substrate.

Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* 65:499–560 (1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° C. to 25° C. in 50 mM Tris (pH 7.6) 50 mM NaCl, 6 mM $MgCl_2$, 6 mM DTT and 5–10 $\mu$M dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with Sl nuclease or Bal-31 results in hydrolysis of any single-stranded portion.

Ligations are performed in 10–50 Al volumes under the following standard conditions and temperatures using T4 DNA ligase. Ligation protocols are standard (D. Goeddel (ed.) Gene Expression Technology: Methods in Enzymology (1991)). In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, religation can be prevented in vectors which have been double digested by additional restriction enzyme digestion of the unwanted fragments.

Suitable vectors include viral vector systems e.g. ADV, RV, and AAV (R. J. Kaufman "Vectors used for expression in mammalian cells" in *Gene Expression Technology,* edited by D. V. Goeddel (1991).

Many methods for inserting functional DNA transgenes into cells are known in the art. For example, non-vector methods include nonviral physical transfection of DNA into cells; for example, microinjection (DePamphilis et al., *BioTechnique* 6:662–680 (1988)); liposomal mediated transfection (Felgner et al., *Proc. Natl. Acad. Sci. USA,* 84:7413–7417 (1987), Felgner and Holm, *Focus* 11:21–25 (1989) and Felgner et al., *Proc. West. Pharmacol. Soc.* 32: 115–121 (1989)) and other methods known in the art.

Administration of Modified Vectors Into Subject

One way to get DNA into a target cell is to put it inside a membrane bound sac or vesicle such as a spheroplast or liposome, or by calcium phosphate precipitation ($CaPO_4$) (Graham F. and Van der Eb, A., Virology 52:456 1973; Schaefer-Ridder M., et al., Liposomes as gene carriers: Efficient transduction of mouse L cells by thymidine kinase gene. *Science* 1982; 215:166; Stavridis J. C., et al., Construction of transferrin-coated liposomes for in vivo transport of exogenous DNA to bone marrow erythroblasts in rabbits. *Exp Cell Res* 1986; 164:568–572).

A vesicle can be constructed in such a way that its membrane will fuse with the outer membrane of a target cell. The vector of the invention in vesicles can home into the prostate cells.

The spheroplasts are maintained in high ionic strength buffer until they can be fused through the mammalian target cell using fusogens such as polyethylene glycol.

Liposomes are artificial phospholipid vesicles. Vesicles range in size from 0.2 to 4.0 micrometers and can entrap 10% to 40% of an aqueous buffer containing macromolecules. The liposomes protect the DNA from nucleases and facilitate its introduction into target cells. Transfection can also occur through electroporation.

Before administration, the modified vectors are suspended in complete PBS at a selected density for injection. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the prostate, is relatively non-traumatic, allows multiple administrations simultaneously in several different sites or the same site using the same viral suspension. Multiple injections may consist of a mixture of therapeutic genes.

Survival of the Modified Vectors So Administered

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., *Cell* 27:299 (1981); Corden et al., *Science* 209:1406 (1980); and Breathnach and Chambon, *Ann. Rev. Biochem.* 50:349 (1981)).

For retroviruses, control elements involved in the replication of the retroviral genome reside in the long terminal repeat (LTR) (Weiss et al., eds., In: The molecular biology of tumor viruses: RNA tumor viruses, Cold Spring Harbor Laboratory, Cold Spring Harbor, N.Y. (1982)).

Moloney murine leukemia virus (MLV) and Rous sarcoma virus (RSV) LTRs contain promoter and enhancer sequences (Jolly et al., *Nucleic Acids Res.* 11:1855 (1983); Capecchi et al., In: Enhancer and eukaryotic gene expression, Gulzman and Shenk, eds., pp. 101–102, Cold Spring Harbor Laboratories, Cold Spring Harbor, N.Y.).

Promoter and enhancer regions of a number of non-viral promoters have also been described (Schmidt et al., *Nature* 314:285 (1985); Rossi and de Crombrugghe, *Proc. Natl. Acad. Sci. USA* 84:5590–5594 (1987)).

The present invention provides methods for maintaining and increasing expression of therapeutic genes using a prostate specific promoter.

In addition to using viral and non-viral promoters to drive therapeutic gene expression, an enhancer sequence may be used to increase the level of therapeutic gene expression. Enhancers can increase the transcriptional activity not only of their native gene but also of some foreign genes (Armelor, *Proc. Natl. Acad. Sci. USA* 70:2702 (1973)).

For example, in the present invention, CMV enhancer sequences are used with the PSA promoter to increase therapeutic gene expression. Therapeutic gene expression may also be increased for long term stable expression after injection using cytokines to modulate promoter activity.

The methods of the invention are exemplified by preferred embodiments in which modified vectors carrying a therapeutic gene are injected intracerebrally into a subject.

In a first embodiment a protein product is expressed comprising growing the host vector system of the invention so as to produce the protein in the host and recovering the protein so produced. This method permits the expression of genes of interest in both unicellular and multicellular organisms. For example, in an in vitro assay, prostate cells having the vector of the invention comprising a gene of interest (e.g., the ras gene) may be used in microtiter wells as an unlimited for the ras gene product. A sample from a subject would be added to the wells to detect the presence of antibodies directed against the ras gene. This assay can aid in the quantitative and qualitative determination of the presence of ras antibodies in the sample for the clinical assessment of whether the subject's immune system is combatting the disease associated with elevated levels of ras.

In a second embodiment metastatic prostate cancer is treated via gene therapy, i.e., the correction of a disease phenotype in vivo through the use of the nucleic acid molecules of the invention.

In accordance with the practice of this invention, the subject of the gene therapy may be a human, equine, porcine, bovine, murine, canine, feline, or avian subject. Other warm blooded animals are also included in this invention.

The most effective mode of administration and dosage regimen for the molecules of the present invention depends upon the exact location of the prostate tumor being treated, the severity and course of the cancer, the subject's health and response to treatment and the judgment of the treating physician. Accordingly, the dosages of the molecules should be titrated to the individual subject. The molecules may be delivered directly or indirectly via another cell, autologous cells are preferred, but heterologous cells are encompassed within the scope of the invention.

The interrelationship of dosages for animals of various sizes and species and humans based on mg/m$^2$ of surface area is described by Freireich, E. J., et al. Cancer Chemother., Rep. 50 (4):219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided dose may be administered daily or proportionally reduced depending on the specific therapeutic situation).

It would be clear that the dose of the molecules of the invention required to achieve cures may be further reduced with schedule optimization.

Advantages of the Invention

The PSA promoter of the invention exhibits prostate tissue specificity. Further, addition of a CMV promoter in the 5' end of the PSA promoter increases the promoter activity by 4–5 folds without compromising its tissue specificity. Since the PSA promoter of the invention is tissue-specific it can only be activated in the targeted tissue, i.e., the prostate. Therefore, the genes of interest driven by the PSA promoter will be differentially expressed in these cells, minimizing systemic toxicity.

In order that the invention described herein may be more fully understood, the following examples are set forth. It should be understood that these examples are for illustrative purposes only and are not to be construed as limiting the scope of this invention in any manner.

EXAMPLE 1

Cloning and characterizing a 620-base pair (bp) fragment (FIG. 10) of DNA derived from the 5' flanking region of the prostate-specific antigen (PSA) gene: We designed two oligonucleotide primers TTG TTT GCG GCC TGG ATT T (SEQ ID NO: 1) and GAC ACA GCT CTC CGG GTG CAG (SEQ ID NO: 2) for polymerase chain reaction (PCR) amplification using a DNA template isolated from a prostate tumor. A DNA fragment of approximately 660 base pairs (bp) was obtained and cloned into an M13mpBM21 phage (Boehringer Mannheim Biochemicals, Indianapolis, Ind.).

Sequencing analysis indicated that this clone is similar to the sequence shown in Genbank, with 7 nucleotide variations. To assess the activity of the fragment, we constructed three plasmids.

Figure 2:
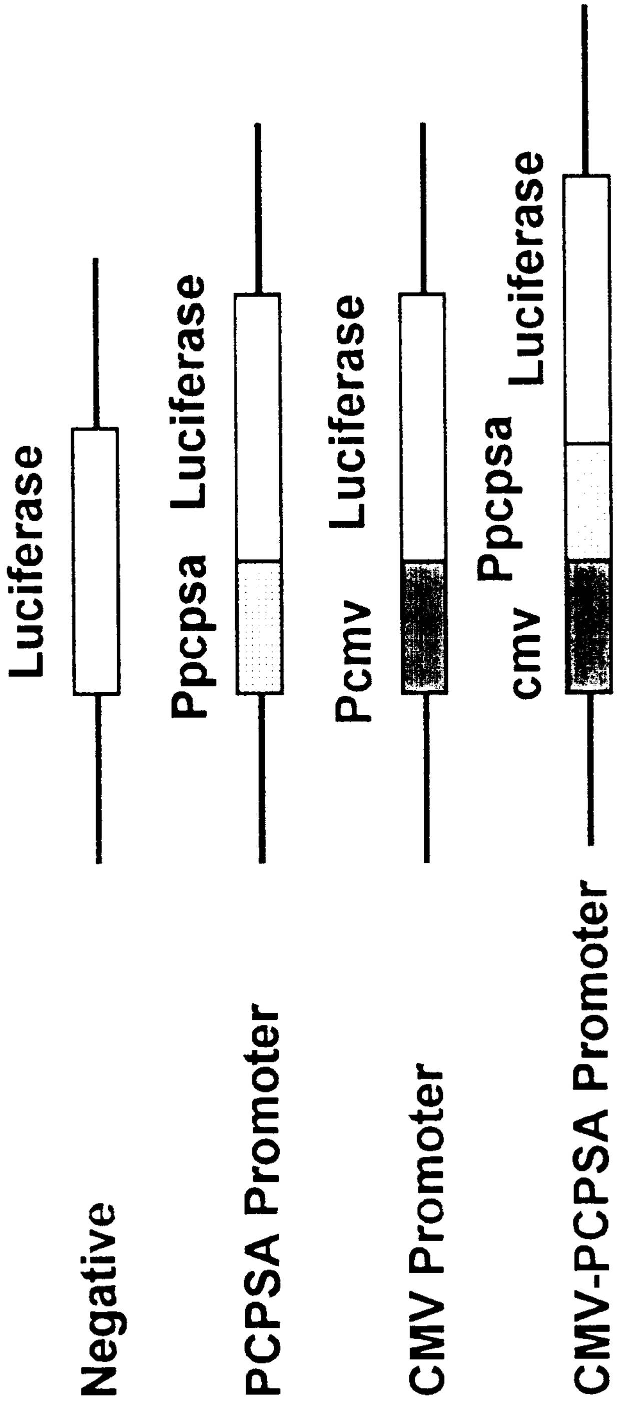
FIG. 2 is a schematic diagram showing the PSA, CMV and CMV-PSA promoters.

The first plasmid was created by inserting our PC-PSA promoter into the 5' end of the firefly luciferase gene within the plasmid pUCMB20 (FIG. 2). The other two plasmids with similar structure containing either the cytomegalovirus (CMV) promoter or no promoter upstream to the luciferase gene (FIG. 2) were used as positive and negative controls respectively.

In FIG. 2 the PC-PSA, CMV and CMV-PC-PSA promoters were cloned to the plasmid puCBM20 (Boehringer Mannheim Biochemicals). The 660-bp PC-PSA promoter obtained through PCR was also cloned to m13BM21 (from BMB also), and the first 150 bp were sequenced. DNA fragment of the PC-PSA promoter 613/+8 (621 bp) was recovered from sequenced clones and inserted into pUCBM20 and BM21 plasmids. CMV IE1 promoter and Luciferase gene were from the plasmid pAC-CMV-Luc. The DNA fragment from BgIII to HindIII sites of the PC-PSA promoter was inserted to the HindIII site of the CMV-Luciferase construct to make the plasmid with CMV-PC-PSA promoter.

Using these three plasmids, we transfected LNCaP (Horoszewicz, J. S. et al., *Progress in Clinical and Biological Research* 37, 115 (1980)) and R11 cells (A. Belldegrun et al., *Journal of the National Cancer Institute* 85, 207 (1993)) by electroporation. Cells were trypsinized and washed with 1xPBMI with 20% fetal bovine serum twice. The cells were resuspended in the same medium to $2\times10^7$ cells/ml. 0.5 ml cell suspension was mixed 20 $\mu$g DNA in ice for 10 minutes before electroporation. The cells were pulsed at 230 volts with 960 mF by using Bio-Rad Gene Pulser (Bio-Rad, Hercules, Calif.). The treated cells were kept in ice for another 10 minutes before replating in regular medium. At 24 hours, the plates were washed with medium once before add new culture medium. Cells were collected at 48 hours post transfection with 1x tissue lysis buffer provided by the luciferase assay kit purchased from Promega (Madison, Wis.) and the cell lysates were assayed by luminometer to measure the activity of firefly luciferase. The plasmid containing the CMV promoter showed increased luciferase activity in both cell lines, whereas the plasmid without a promoter demonstrated very low expression of luciferase. Compared to negative control, the PC-PSA promoter exhibited more than fifty-fold increase in luciferase expression in LNCaP cells as compared to only two- to three-fold increase in luciferase activity in R11 cells (FIG. 3).

Figure 3:
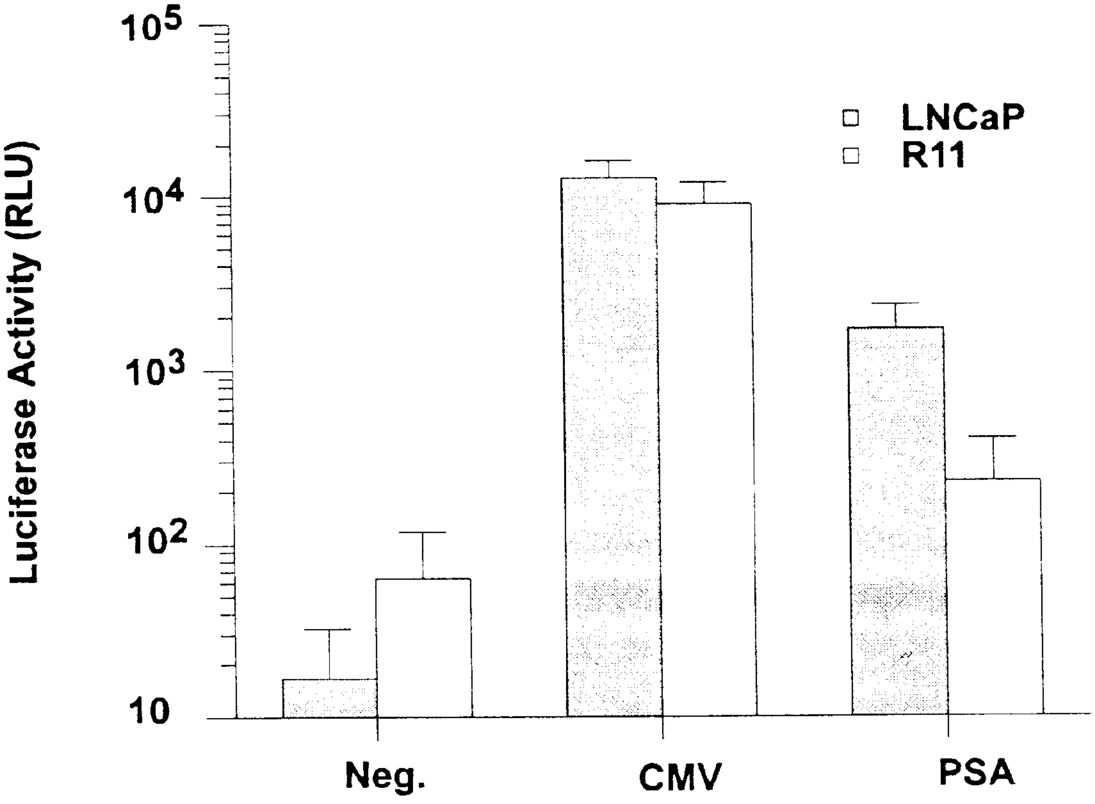
FIG. 3 is a bar graph showing luciferase activity in LNCaP and R11 cells after DNA transfection of electroporation.

In FIG. 3 luciferase activity was assayed in LNCaP and R11 cells after DNA transfection of electroporation. Cells were trypsinized and washed with 1xPBMI with 20% fetal bovine serum twice. The cells were resuspended in the same medium to $2\times10^7$ cells/ml. 0.5 ml cell suspension was mixed 20 $\mu$g DNA in ice for 10 minutes before electroporation. The cells were pulsed at 230 volts with 960 mF by using Bio-Rad Gene Pulser (Bio-Rad, Hercules, Calif.). The treated cells were kept in ice for another 10 minutes before replating in regular medium. At 24 hours, the plates were washed with medium once before add new culture medium. Cells were collected at 48 hours post transfection with 1x tissue lysis buffer provided by the luciferase assay kit purchased from Promega (Madison, Wis.) and the cell lysates were assayed by luminometer to measure the activity of firefly luciferase. The scale of luciferase activity is in logarithmic format.

Luciferase expression from the PC-PSA-promoter driven plasmid is approximately 50-fold higher than the negative control in LNCaP cells. However, only a two- to three-fold increase in luciferase activity was demonstrated in renal R11 cells. Luciferase activity was measured as raw light units (RLU) per microgram cellular protein.

Determining the effects of varying the androgen concentration on the activity of the cloned promoter. LNCaP cells were grown in culture medium with 10% charcoal-stripped fetal bovine serum (cFBS) for six days prior to transfection. After transfection, dihydrotestosterone (DHT) was added to the culture medium in concentrations ranging from 0 to 1 mM DHT. A DHT concentration of 10 $\mu$M in the culture medium increased luciferase expression approximately 50-fold (FIG. 4).

Figure 4:
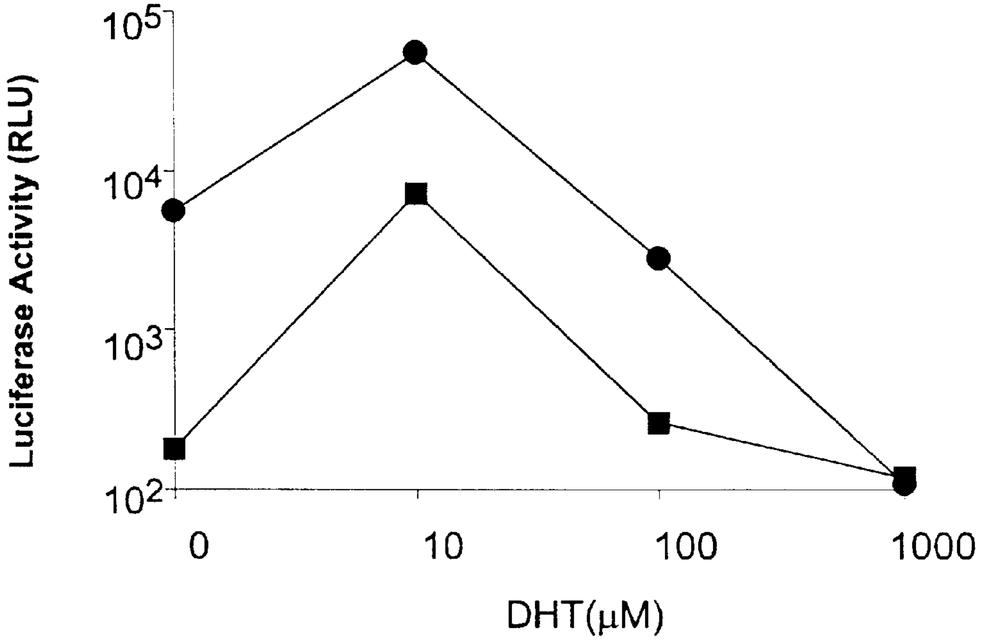
FIG. 4 is a line graph showing that both the CMV (●) and PSA (■) promoters were responsive to androgen.

In FIG. 4 both the CMV and PC-PSA promoters were responsive to androgen. LNCaP cells were grown in medium containing 10% CFBS for 6 days prior to electroporation. The procedure to prepare CFBS was as follows: 0.625 gram charcoal (Mallinckrodt) and 12.5 mg of dextran sulfate were washed with 500 ml of phosphate-buffered saline (PBS) once before being mixed (by shaking or Vortex of 30 minutes) with 500 ml fetal bovine serum. The charcoal was removed from the serum by centrifuge and 0.2 micron filtration. After electroporation, cells were transferred into four 10-cm plates with various concentrations of DHT (0–1000 $\mu$M). The cells were washed and maintained in medium containing the same concentrations of DHT at 16 hours post-transfection. Luciferase activity was measured as RLU per microgram cellular protein isolated from cells transfected by plasmid containing either CMV promoter (●) or plasmid containing PC-PSA promoter (■).

Activity of the CMV promoter increased with the addition of DHT, suggesting that elements responsive to androgen were present within the CMV promoter (FIG. 4). The CMV promoter contains an enhancer of 405 bp, a TATA-box, and 80 bp of linking sequences. The total length is approximately 600 bp. Through DNA sequence analysis, neither an ARE nor another hormone-responsive element (HRE) could be identified. The activation by androgen therefore may not require directed binding of androgen receptor to the CMV promoter.

To increase the PC-PSA promoter activity, we have added a CMV enhancer element upstream to the PC-PSA promoter. The CMV promoter was selected because of its potency and responsiveness to androgen (FIG. 4). A fraction of the CMV promoter sequence, with the entire enhancer and TATA-box was added to the 5' end of PC-PSA promoter to create a new promoter, the CMV-PC-PSA promoter (FIG. 2).

Characterization of the CMV-PC-PSA construct: The newly constructed expression cassette was then tested in the prostate cell lines LNCaP, DU145, and PC-3 with the kidney cell line R11 as a control. DU145 and PC-3, express very low level of androgen receptor (W. D. Tilley et al., *Cancer Research* 50, 5382 (1990)), and were thus utilized to help elucidate the role of the androgen receptor in the activation of the PC-PSA promotor. The CMV-PC-PSA promoter demonstrated very low activity in R11 cells, as did the PC-PSA promoter and the negative control plasmids (FIG. 5*b*). In the LNCaP cells, however, CMV-PC-PSA promoter activity was four- to five-fold higher than that of the PC-PSA promoter alone (FIG. 5*a*), confirming that the addition of a strong enhancer region can increase the PC-PSA promoter activity.

Figure 5A:
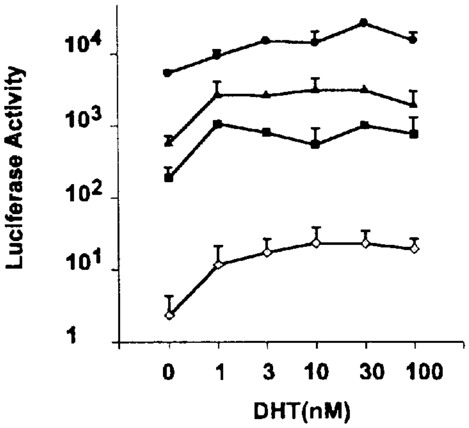
FIGS. 5*a/b/c/d/e* are line graphs showing luciferase activity. Panel a) LNCaP, b) R11, c) MCF-7, d) PC-3, e) DU145. Luciferase activity was measured as RLU units per microgram cellular protein isolated from cells transfected by plasmid containing CMV promoter (●), plasmid containing PSA promoter (■), plasmid with CMV-PSA promoter (▲) and plasmid with no promoter as negative control (♦).
Figure 5B:
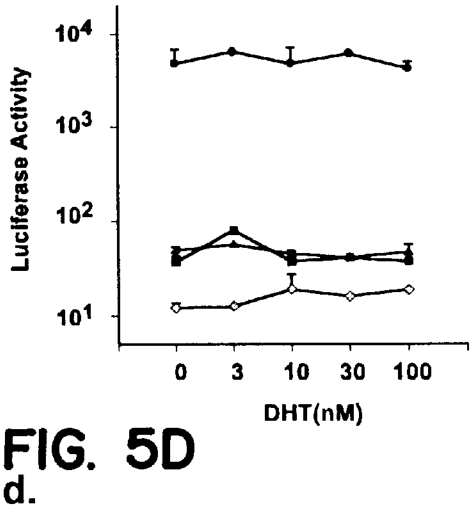

In FIGS. 5*a*/*b*/*c*/*d*/*e* cells were transfected with plasmids containing different promoters and grown in different concentrations of DHT. Cells were transferred from regular medium to the medium with CFBS for 3 days prior to electroporation. Cells were trypsinized from plates and washed twice with electroporation (EP) medium. 100 ml EP medium contains 96 ml 1xRPMI medium with 10% CFBS and 4 ml 5XRPMI. The washed cell were resuspended in EP medium to $2\times10^7$ cells/ml. DNA of 20 $\mu$g were added to 0.5 ml cells for each electroporation. After electroporation the transfected cells were plated to six-well plate within medium containing 10% CFBS and varying concentrations of DHT. At 16 hours, the cells were washed once and maintained in the same medium. At 48 hours, cells were lysed and assayed for luciferase activity. Panel a) LNCaP, b) R11, c) MCF-7, d) PC-3, e) DU145. Luciferase activity was measured as RLU units per microgram cellular protein isolated from cells transfected by plasmid containing CMV promoter (●), plasmid containing PC-PSA promoter (■), plasmid with CMV-PC-PSA promoter (▲) and plasmid with no promoter as negative control (♦).

Figure 5C:
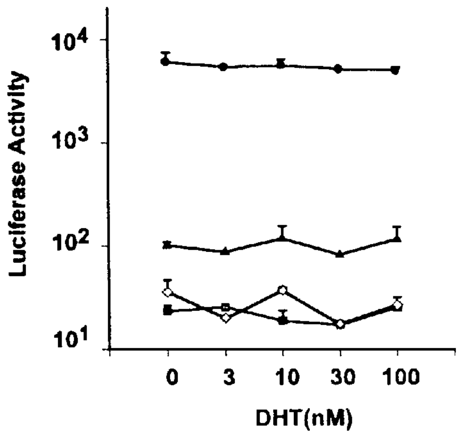
Figure 5D:
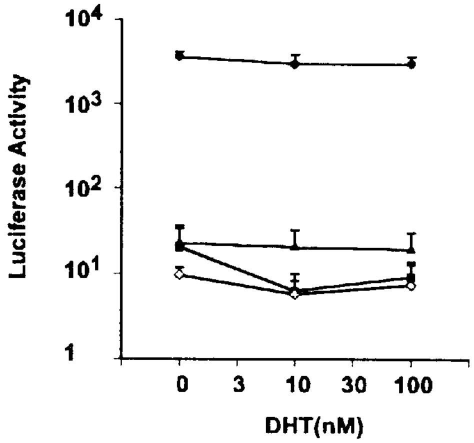
Figure 5E:
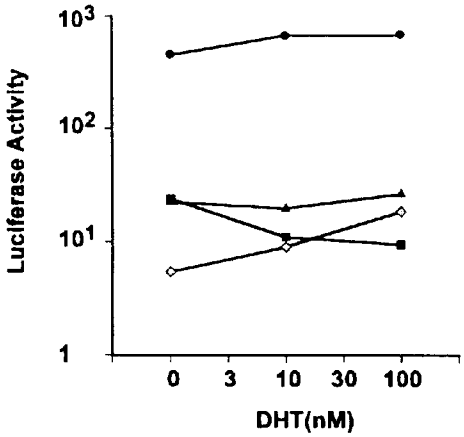
Figure 6:
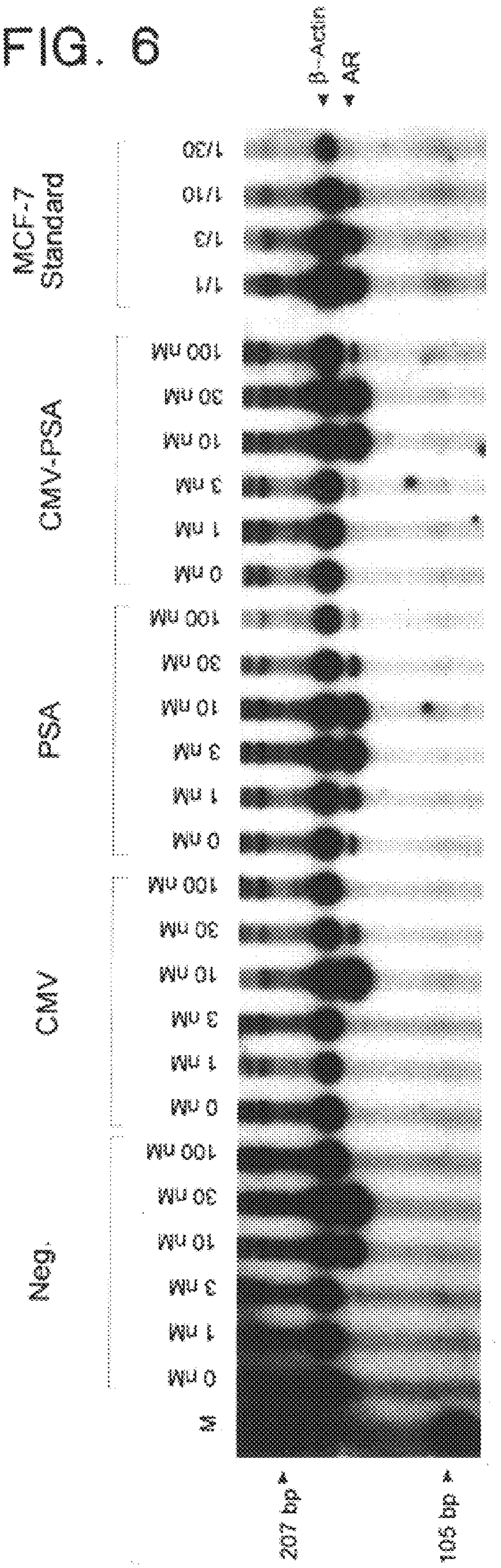
FIG. 6 are gels showing RNA quantitation of MCF-7 cells exposed to DHT. The highest expression of androgen receptor (AR) presented in the cells grown in the medium containing 3 to 30 nM DHT.

Cell transfections were performed under similar conditions as described in the legend of FIG. 4 with some modifications. Transfected cells were maintained in media with 0 to 100 nM DHT rather than 0 to 1000 μM in 10% CFBS, concentrations of DHT which are comparable to that of the human body (Prostate Diseases, ed. by H. Lepor and R. K. Lawson. W. B. Saunders Company, Philadelphia, Pa. (1993)). In the PC-3 and DU-145 cell lines, neither the PC-PSA promoter nor the CMV-PC-PSA promoter responded to DHT (FIGS. 5*d* and 5*e*). The absence of the androgen receptor in these cells abrogated the responsiveness of PC-PSA promoter to androgen stimulation. In the LNCaP cells, however, PC-PSA promoter activity increased with the addition of DHT, as expected. The highest activity was demonstrated at concentrations of 3 nM to 30 nM of DHT, paralleling that of the physiologic range of DHT (4.5–18 nM). Using quantitative PCR, we determined that the maximum expression of AR mRNA corresponded to the 3 to 30 nM range of DHT added to the LNCaP cultures (FIG. 6). The AR mRNA expression profile was consistent with the activities of the PC-PSA and the CMV-PC-PSA promoters.

In FIG. 6 transfected LNCaP cells were lysed for RNA quantitation. The RNA was purified and reverse transcribed to cDNA. In parallel, RNA was isolated from $10^6$ MCF-7 cells and reverse transcribed as a control. The cDNA obtained was utilized for PCR quantitation. β-actin cDNA served as the internal control to evaluate the quantity of RNA and to normalize cDNA samples. Most cDNA samples showed similar β-actin mRNA level equivalent to those found in a 1/10 dilution of MCF-7 (around $10^5$ cells) . The highest expression of androgen receptor (AR) presented in the cells grown in the medium containing 3 to 30 nM DHT. Detectable amounts of AR mRNA were also shown in MCF-7 cells.

The breast cancer cell line MCF-7 (Catalogue of Cell Lines & Hybridomas. American Type Culture Collection (ATCC). eds. R. Hay et al., 6th ed., 1988. Rockville, Md.) was utilized to investigate the significance of the AR on PC-PSA promoter activity. PCR quantitation indicated that the androgen receptor gene was transcribed in MCF-7 cells (FIG. 6). As depicted in FIG. 5*c*, the PC-PSA promoter and the CMV-PC-PSA promoter did not show significant promoter activity in any DHT concentrations in these cells, suggesting that the activation of the PC-PSA promoter appears to depend not only upon AR, but also upon other promoter DNA binding proteins produced exclusively in prostate cells.

Figure 7:
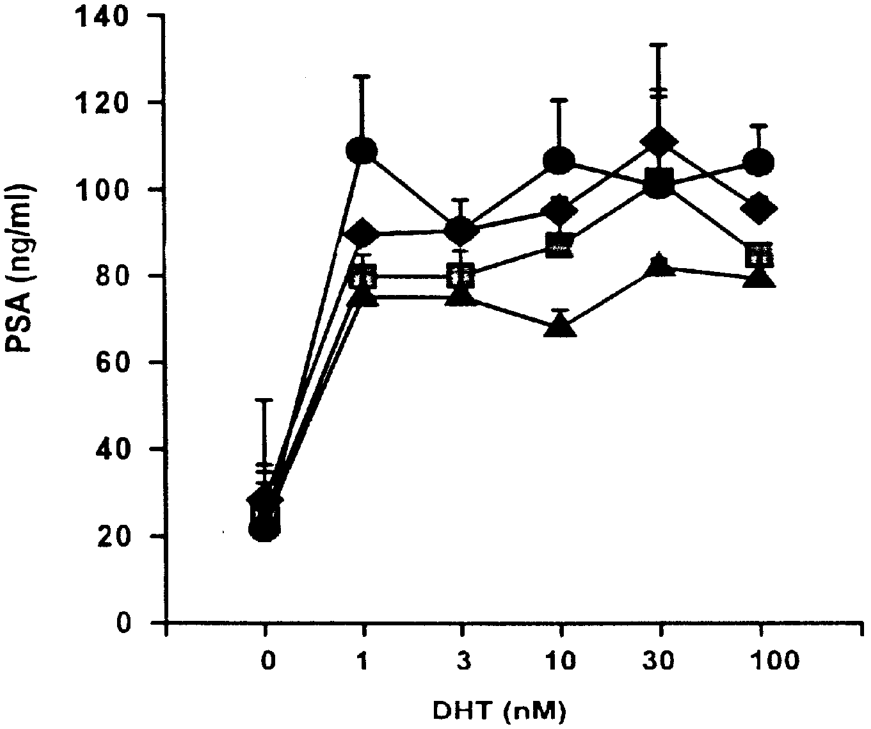
FIG. 7 is a line graph showing that PSA and CMV-PSA promoters (SEQ ID NO: 3) significantly inhibited the expression of PSA in LNCaP cells. LNCaP cells were transfected with plasmid containing the CMV promoter (●), the PSA promoter (■), the CMV-PSA promoter (▲), and plasmid without promoter (♦) for PSA quantification by IMX immunoassay analyzer (Abbott Laboratories, North Chicago, Ill.).

We investigated whether the cloned PC-PSA promoter competitively inhibits the endogenous genomic PC-PSA promoter. The amount of PC-PSA protein produced by the plasmid transfected LNCaP cells in the presence of varying concentrations of DHT was quantified. PC-PSA was measured using IMX automated immunoassay analyzer with MEIA kit. Both were provided by Abbott Diagnostics, Abbott Park, Ill. A significant decrease in PC-PSA secreted by cells transfected with either PC-PSA or CMV-PC-PSA plasmids was demonstrated (FIG. 7). This decrease in PC-PSA production was however more pronounced with the CMV-PC-PSA promoter, consistent with its higher promoter activity. This suggests that PC-PSA-producing prostate cells contains a DNA binding protein which is highly specific to the PC-PSA promoter.

In FIG. 7 both PC-PSA and CMV-PC-PSA promoters significantly inhibited the expression of PC-PSA in LNCaP cells. Two days post transfection, 200 μl of medium were taken from culture plates with the cells transfected by plasmid containing the CMV promoter (●), the PC-PSA promoter (■), the CMV-PC-PSA promoter (▲), and plasmid without promoter (♦) for PC-PSA quantification by IMX immunoassay analyzer (Abbott Laboratories, North Chicago, Ill.).

Figure 8:
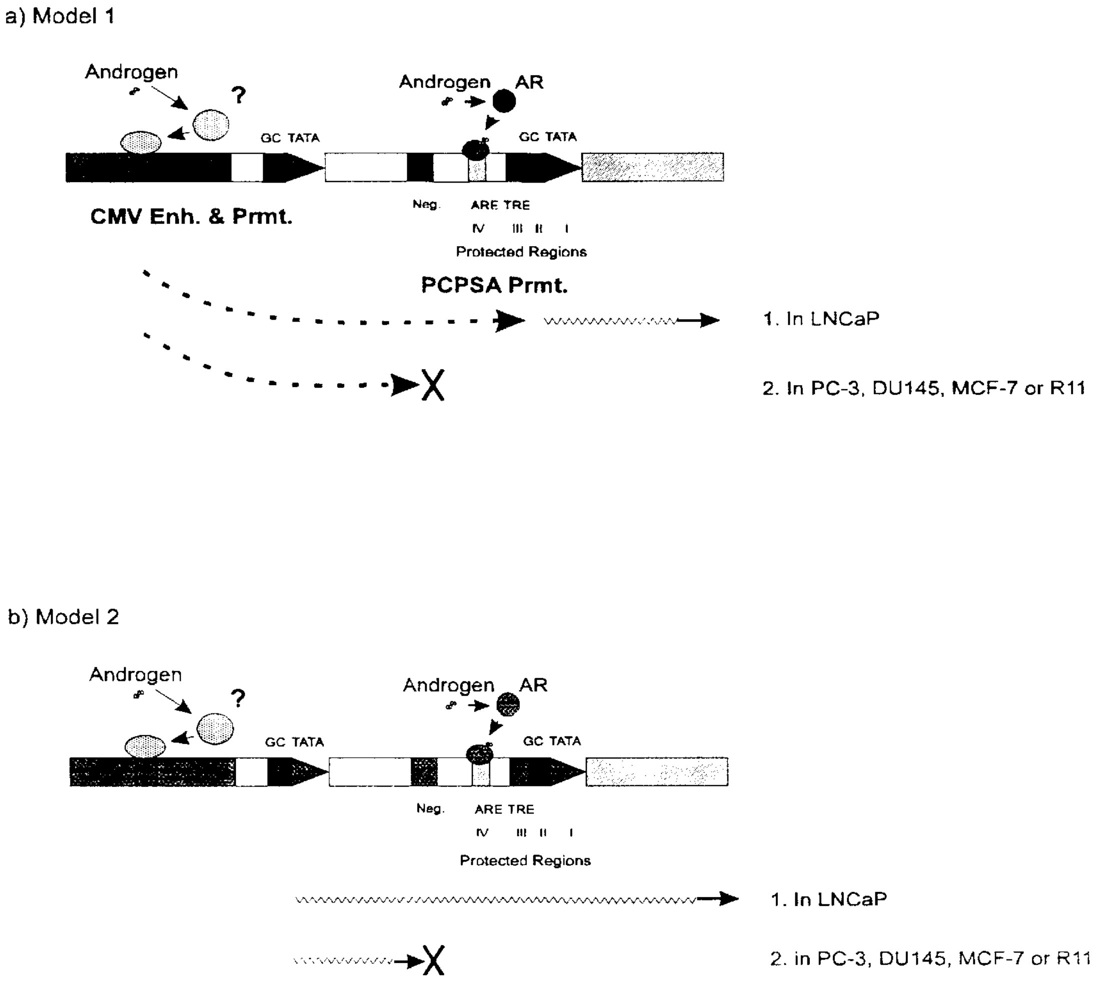
FIG. 8 is a schematic diagram of two models explaining the tissue specificity of the CMV-PSA promoter (SEQ ID NO: 7).

FIG. 8 provides two models to explain the tissue specificity of the CMV-PC-PSA promoter. In panel (a) Model 1: RNA transcription starts at the TATA box of PC-PSA promoter. The negative (Neg.) elements may simply block the interaction between the CMV enhancer and the GC-box or TATA-box of the PC-PSA promoter in non-PC-PSA-producing cells (PC-3, DU145, MCF-7 or R11).

In panel (b) Model 2: RNA transcription starts at the TATA-box within the CMV promoter. However, the transcription is terminated at the location of the negative elements in the PC-PSA promoter in non-PC-PSA-producing cells.

The CMV-PC-PSA promoter contains two transcriptional initiation sites (FIG. 8), one in the 3' of the PC-PSA promoter and one in the 3' of the CMV sequence. The CMV-PC-PSA promoter specificity can be explained by one of two models. In the first model, we presume that the TATA-box in the CMV sequence does not function as a transcriptional initiation site. Instead, the CMV sequence provides only an enhancer function to gene transcription. Alternately, in model 2, we presume that transcription starts at the TATA-box in the CMV sequence region. The RNA transcription continues through the PC-PSA promoter in PC-PSA-producing cells (LNCaP) but not in non-PC-PSA producing cells (DU-145 and PC-3, R11 and MCF-7). A negative regulatory element is suggested by both models. As the 3' 245 bp sequence of PC-PSA promoter that contains the TATA-box, the GC-box, the TPA-responsive element (TRE), and the ARE has already been well characterized (6), the most likely location of the negative regulatory element is in the 5' region of the PC-PSA promoter. A detailed study to identify the control mechanisms of the PC-PSA and CMV-PC-PSA promoters is currently underway using deletions of the TATA-boxes in the region of either PC-PSA promoter or CMV-PC-PSA promoter sequences and by Northern blotting to define the size of transcripts.

Genes specifically expressed in prostate cells have been identified in both humans and rodents (G. Watson and K. Paigen, *Molecular and Cellular Endocrinology* 68, 67 (1990); M. Izawa, *Endocrinology Japonica* 37, 223 (1990); A. Crozat et al., *Endocrinology* 130, 1131 (1992); P. S. Rennie et al., *Molecular Endocrinology* 7, 23 (1993); N. B. Ghyselinck et al., *Molecular Endocrinology* 7, 258 (1993); P. Murtha et al., *Biochemistry* 32, 6459 (1993); L. Celis et al., *Molecular and Cellular Endocrinology* 94, 165 (1993)).

Of these genes, only the PSA gene which is specifically expressed in human prostate tissue cells, has so far been extensively studied. Understanding its unique mechanism of transcriptional control may prove very beneficial in developing a target-specific expression vector for gene therapy of prostate cancer. In this study, we have combined DNA transfection, quantitative mRNA PCR and PC-PSA assays to characterize the role of the PC-PSA promoter in prostate cancer tissue. The results demonstrate that the PC-PSA promoter (1) is prostate-tissue specific; (2) is androgen dependent; (3) requires androgen receptor stimulation; and (4) can be modified by a CMV enhancer region to increase transcriptional activity without losing tissue specificity; (5) requires additional prostate tissue specific PC-PSA promoter-binding proteins. These features of the PC-PSA promoter are fundamental to the development of a target specific vector for treating metastatic prostate cancer via gene therapy. As tumor cells from most patients with hormone refractory metastatic prostate cancer express high levels of mRNA of PC-PSA and androgen receptor, the promoter of the invention will be applicable for therapeutic use in these patients.

In summary, using DNA transfection, the efficacy of the CMV-PC-PSA promoter in regulating gene expression was quantitated in several prostate and non-prostate tissue cell lines. The results demonstrate that the 621-bp DNA fragment actively drives gene expression in LNCaP, a PC-PSA-producing prostate tumor line. No promoter activity was detected in the non-PC-PSA-producing prostate tumor lines, DU145 and PC-3, nor in a renal (R11) or breast (MCF-7) cell line. Furthermore, PC-PSA promoter activity could be regulated in vitro by androgen stimulation (C. Y. Young et al., *Cancer Research* 51, 3748 (1991); C. J. Fong et al., *Prostate* 21, 121 (1992); P. Henttu et al., *Endocrinology* 130, 766 (1992)). Dihydrotestosterone (DHT) concentrations between 3 and 30 nM induced the highest promoter activity in the transfected LNCaP cells, which parallels PC-PSA secretion into culture media by transfected LNCaP cells. In addition, the PC-PSA promoter of the invention exhibited competitive inhibition of the endogenous genomic PC-PSA promoter in transfected LNCaP cells. A cytomegalovirus IE1 promoter (CMV promoter) attached into the 5' flanking region of the PC-PSA promoter increased its potency four- to five-fold while retaining its tissue specificity. The data suggest that a strong tissue-specific negative regulatory element capable of overriding the nonspecific CMV promoter is present in the PC-PSA promoter, and confers its tissue specificity.

EXAMPLE 2

Figure 12:
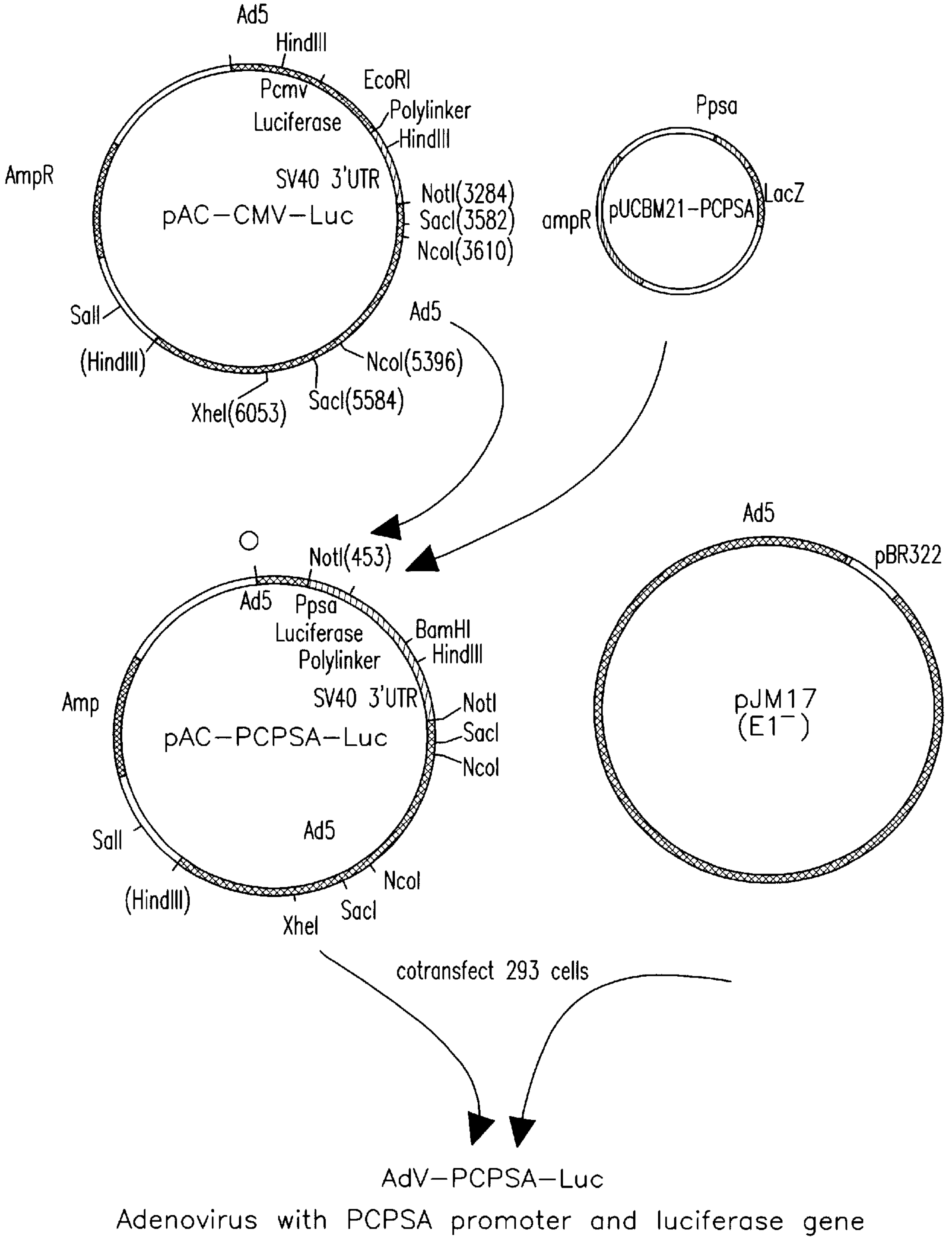
FIG. 12 is a schematic diagram showing the construction of an adenoviral vector with PCPSA promoter and Luciferase gene. The PCPSA promoter was obtained from pBM21-PCPSA plasmid. The DNA fragment was then used to replace the CMV promoter in the plasmid pAC-CMV-Luc. The resulted plasmid pAC-PCPSA-Luc was cotransfected with plasmid pJM17 into 293 human cells. The recombination between these two plasmids in the 293 cells will generate an adenovirus with PCPSA promoter and Lux gene.

The prostate tissue specific promoter PCPSA was cloned into an adenoviral vector (FIG. 12). This adenoviral vector AdV-PCPSA-Luc was tested using severe combined immunodeficient (SCID) mice carrying prostate tumors derived from a patient RM. Strong tissue specificity was demonstrated (Table 1).

Figure 13:
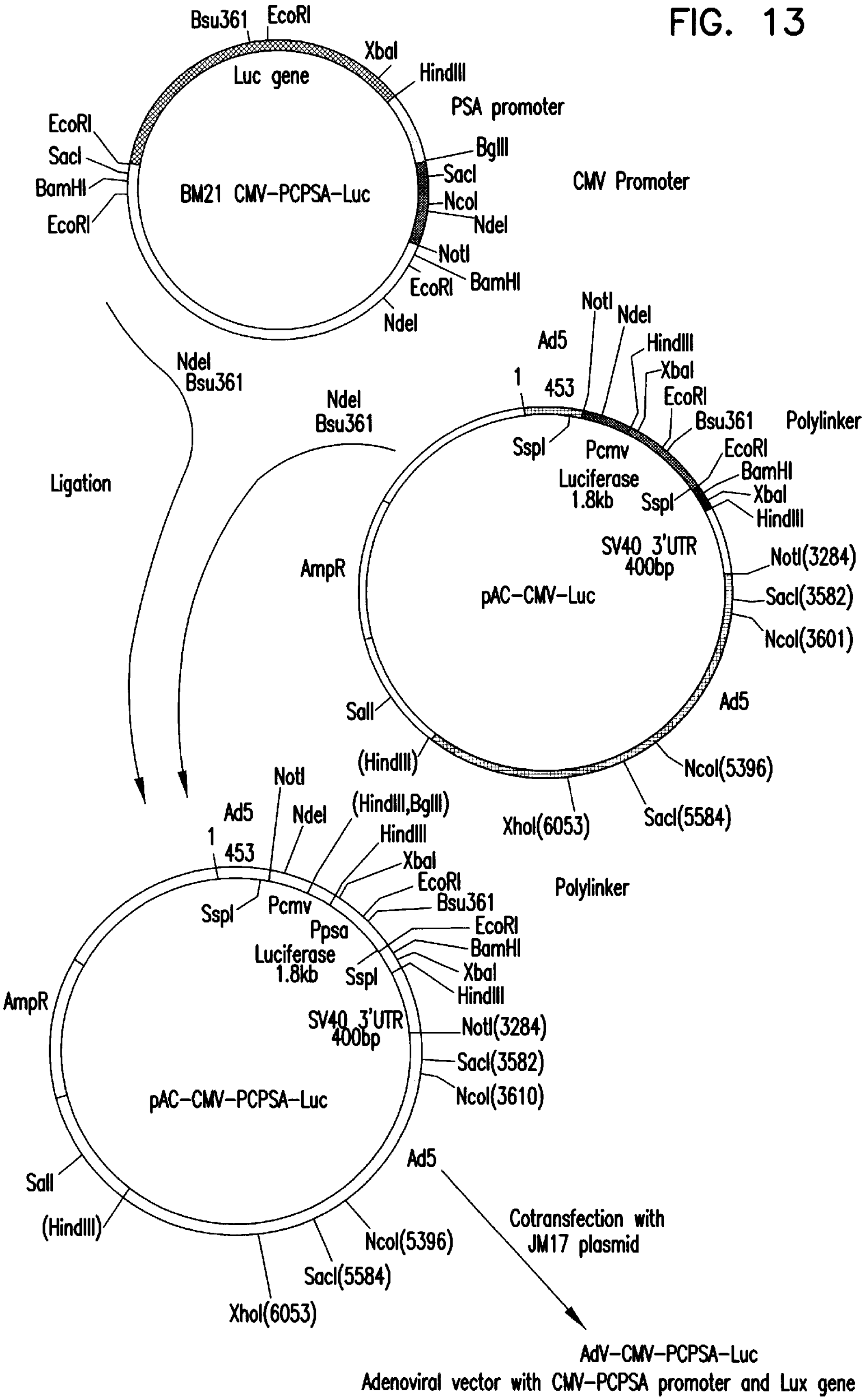
FIG. 13 is a schematic diagram showing the construction of an adenoviral vector with CMV-PCPSA promoter and luciferase gene.

We modified the PCPSA promoter by adding a enhancement sequence from cytomegalovirus (CMV) immediate early gene promoter I (IE1). The CMV IE1 enhancer has shown its enhancement effect in our early DNA transfection tests. The CMV enhancer modified PCPSA promoter was cloned into an adenoviral vector (FIG. 13). SCID mice carrying prostate tumors derived from LNCaP cell line were used. Results demonstrated that the activity of PCPSA was greatly increased, however the specificity was decreased in liver and spleen (Table 2).

Our results of in vivo test demonstrated that the PCPSA promoter is a prostate tissue specific promoter. With the addition of a strong enhancer, the promoter activity can be greatly increased.

TABLE 1

Infection of prostate tumor carried by severe combined immunodeficient (SCID) mice. Adenovirus with PCPSA promoter and luciferase gene of $10^9$ pfu was injected to the tumors. One day post the infection the mice were sacrified and organs and the tumor tissue were saved for luciferase assay. Since the background (water) luciferease activity is 149–198 RLU, the organs with luciferase activity less than 250 are considered not significant (i.e. luciferase activity was undetectable).

| samples | | | # | Lux |
|---|---|---|---|---|
| | Mouse | Inj. | 1 | 1,807 |
| | | Kidney | 2 | 213 |
| | | Spleen | 3 | 158 |
| | | Lung | 4 | 271 |
| | | brain | 5 | 154 |
| | | heart | 6 | 147 |
| | | Liver | 7 | 152 |
| | Mouse | Inj. | 8 | 1,313 |
| | | Kidney | 9 | 163 |
| | | Spleen | 10 | 183 |
| | | Lung | 11 | 228 |
| | | brain | 12 | 177 |
| | | heart | 13 | 158 |
| | | Liver | 14 | 220 |
| | water | | 15 | 198 |
| | | | 16 | 149 |

TABLE 2

AdV-CMV-PCPSA-Luc adenoviral vector was used to infect LUCaP tumors carried by SCID mice. LNCaP prostate tumor line was transplanted to two sides of each SCID mouse subcutaneously. Virus of $10^9$ pfu was injected into the one tumor location of each mouse. At day 4 and day 10, the mice were sacrificed. Tumor tissues and mouse organs were save for luciferase assay. The luciferase activity was presented RLU/μg protein. RLU: Raw light unit.

| SCID mice with LNCaP | | | | | |
|---|---|---|---|---|---|
| Day | | tissue | # | lucifera | RLU/μg |
| day 4 | Mouse 1 | Inj. | 1 | 1,899,94 | 36,679.72 |
| | | Uninj. | 2 | 511 | 10.46 |
| | | Prostate | 3 | 441 | 9.4 |
| | | Parotid | 4 | 374 | 8.74 |
| | | Kidney | 5 | 310 | 8.98 |
| | | Spleen | 6 | 1,534 | 62.85 |
| | | Lung | 7 | 231 | 5.22 |
| | | brain | 8 | 199 | 4.38 |
| | | Liver | 9 | 108,654 | 2,486.88 |
| | Mouse 2 | Inj. | 10 | 1,544,74 | 43,044.67 |
| | | Uninj. | 11 | 30,005 | 1,636.90 |
| | | Prostate | 12 | 41,565 | 1,964.19 |
| | | Parotid | 13 | 1,208 | 54.44 |
| | | Kidney | 14 | 4,104 | 291.77 |
| | | Spleen | 15 | 35,074 | 1,954.90 |
| | | Lung | 16 | 2,688 | 127.16 |
| | | brain | 17 | 549 | 43.53 |
| | | Liver | 18 | 244195 | 6,802.19 |
| day 10 | Mouse 1 | Inj. | 1 | 412,739 | 13,754.63 |
| | | Kidney | 2 | 134 | 1.13 |
| | | Lung | 3 | 122 | 0.73 |
| | | Soft | 4 | 183 | 2.77 |
| | | Prostate | 5 | 156 | 1.87 |
| | | brain | 6 | 172 | 2.4 |
| | | Liver | 7 | 19,988 | 662.93 |
| | | Spleen | 8 | 14,802 | 490.07 |
| | | Uninj. Tu | 9 | 118 | 0.6 |
| | | Parotid | 10 | 2,679 | 85.97 |
| | Mouse 2 | Inj. | 11 | 353,853 | 11,791.77 |
| | | Kidney | 12 | 238 | 4.6 |
| | | Lung | 13 | 548 | 14.93 |
| | | Soft | 14 | 396 | 9.87 |

TABLE 2-continued

AdV-CMV-PCPSA-Luc adenoviral vector was used to infect LUCaP tumors carried by SCID mice. LNCaP prostate tumor line was transplanted to two sides of each SCID mouse subcutaneously. Virus of $10^9$ pfu was injected into the one tumor location of each mouse. At day 4 and day 10, the mice were sacrificed. Tumor tissues and mouse organs were save for luciferase assay. The luciferase activity was presented RLU/μg protein. RLU: Raw light unit.

| SCID mice with LNCaP | | | | |
|---|---|---|---|---|
| Day | tissue | # | lucifera | RLU/μg |
| | Prostate | 15 | 1,862 | 58.73 |
| | brain | 16 | 2,274 | 72.47 |
| | Liver | 17 | 31,416 | 1,043.87 |
| | Spleen | 18 | 32,729 | 1,087.63 |
| | Uninj. Tu | 19 | 323 | 7.43 |
| | Parotid | 20 | 14,803 | 490.1 |

What is claimed is:

1. An isolated nucleic acid molecule having a sequence beginning with guanine at nucleotide position 665 and ending with thymine at nucleotide position 1216 as shown in FIG. 9.

2. An isolated nucleic acid molecule having a sequence beginning with guanine at nucleotide position 70 and ending with thymine at nucleotide position 620 as shown in the top line of FIG. 10.

3. A nucleic acid molecule comprising the nucleic acid molecule of claim 1 or 2 and an enhancer element.

4. The nucleic acid molecule of claim 3, wherein the enhancer element is a portion of the CMV promoter.

5. The nucleic acid molecule of claim 3, wherein the enhancer element is a portion of the MMTV LTR.

6. The nucleic acid molecule of claim 3, wherein the enhancer element is a portion of the SV40 enhancer.

7. The nucleic acid molecule of claim 3, wherein the enhancer element is a portion of the RSV.

8. The nucleic acid molecule of claim 2 or 3 that is a cDNA molecule.

9. A vector having the nucleic acid molecule of claim 2 or 3 and a transgene.

10. A eucaryotic host cell comprising the vector of claim 9.

11. The eucaryotic host cell of claim 10, wherein the compatible eukaryotic host cell is a PSA producing cell.

12. A method for producing a protein comprising growing the host eucaryotic cell of claim 11 so as to produce the protein in the host and recovering the protein so produced.

13. A nucleic acid molecule having the sequence as shown in FIG. 9.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

TTGTTTGCGG CCTGGATTT 19

(2) INFORMATION FOR SEQ ID NO:2:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

GACACAGCTC TCCGGGTGCA G 21

(2) INFORMATION FOR SEQ ID NO:3:

(i) SEQUENCE CHARACTERISTICS:
(A) LENGTH: 1216 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

```
GTCGACATTG ATTATTGACT AGTTATTAAT AGTAATCAAT TACGGGGTCA TTAGTTCATA     60
GCCCATATAT GGAGTTCCGC GTTACATAAC TTACGGTAAA TGGCCCGCCT GGCTGACCGC    120
CCAACGACCC CCGCCCATTG ACGTCAATAA TGACGTATGT TCCCATAGTA ACGCCAATAG    180
GGACTTTCCA TTGACGTCAA TGGGTGGACT ATTTACGGTA AACTGCCCAC TTGGCAGTAC    240
ATCAAGTGTA TCATATGCCA AGTACGCCCC CTATTGACGT CAATGACGGT AAATGGCCCG    300
CCTGGCATTA TGCCCAGTAC ATGACCTTAT GGGACTTTCC TACTTGGCAG TACATCTACG    360
TATTAGTCAT CGCTATTACC ATGGTGATGC GGTTTTGGCA GTACATCAAT GGGCGTGGAT    420
AGCGGTTTGA CTCACGGGGA TTTCCAAGTC TCCACCCCAT TGACGTCAAT GGGAGTTTGT    480
TTTGGCACCA AAATCAACGG GACTTTCCAA AATGTCGTAA CAACTCCGCC CCATTGACGC    540
AAATGGGCGG TAGGCGTGTA CGGTGGGAGG TCTATATAAG CAGAGCTCTC TGGCTAACTA    600
GAGAACCCAC TGCTTAACTG GCTTATCGAA ATTAATACGA CTCACTATAG GGAGACCGGA    660
AGCTGATCTT TTTATGATGA CAGTAGCAAT GTATCTGTGG AGCTGGATTC TGGGTTGGGA    720
GTGCAAGGAA AAGAATGTAC TAAATGCCAA GACATCTATT TCAGGAGCAT GAGGAATAAA    780
AGTTCTAGTT TCTGGTCTCA GAGTGGTGCA GGGATCAGGG AGTCTCACAA TCTCCTGAGT    840
GCTGGTGTCT TAGGGCACAC TGGGTCTTGG AGTGCAAAGG ATCTAGGCAC GTGAGGCTTT    900
GTATGAAGAA TCGGGGATCG TACCCACCCC CTGTTTCTGT TTCATCCTGG GCATGTCTCC    960
TCTGCCTTTG TCCCCTAGAT GAAGTCTCCA TGAGCTACAA GGGCCTGGTG CATCCAGGGT   1020
GATCTAGTAA TTGCAGAACA GCAAGTGCTA GCTCTCCCTC CCCTTCCACA GCTCTGGGTG   1080
TGGGAGGGGG TTGTCCAGCC TCCAGCAGCA TGGGGAGGGC CTTGGTCAGC CTCTGGGTGC   1140
CAGCAGGGCA GGGGCGGAGT CCTGGGGAAT GAAGGTTTTA TAGGGCTCCT GGGGGAGGCT   1200
CCCCAGCCCC AAGCTT                                                   1216
```

(2) INFORMATION FOR SEQ ID NO:4:

(i) SEQUENCE CHARACTERISTICS:
- (A) LENGTH: 620 base pairs
- (B) TYPE: nucleic acid
- (C) STRANDEDNESS: single
- (D) TOPOLOGY: linear (ii) MOLECULE TYPE: protein (xi) SEQUENCE DESCRIPTION: SEQ ID NO:4:

```
TTGGATTTTG AAATGCTAGG GAACTTTGGG AGACTCATAT TTCTGGGCTA GAGGATCTGT     60
GGACCACAAG ATCTTTTTAT GATGACAGTA GCAATGTATC TGTGGAGCTG GATTCTGGGT    120
TGGGAGTGCA AGGAAAAGAA TGTACTAAAT GCCAAGACAT CTATTTCAGG AGCATGAGGA    180
ATAAAAGTTC TAGTTTCTGG TCTCAGAGCG GTGCAGGGAT CAGGGAGTCT CACAATCTCC    240
TGAGTGCTGG TGTCTTAGGG CACACTGGGT CTTGGAGTGC AAAGGATCTA GGCACGTGAG    300
GCTTTGTATG AAGAATCGGG GATCGTACCC ACCCCCTGTT TCTGTTTCAT CCTGGGCATG    360
TCTCCTCTGC CTTTGTCCCC TAGATGAAGT CTCCATGAGC CACAGGGCCT GGTGCATCCA    420
GGGTGATCTA GTAATTGCAG AACAGCAAGT ACTAGCTCTC CCTCCCCTTC CACAGCTCTG    480
GGTGTGGGAG GGGGTTGTAC AGCCTCCAGC AGCATGGAGA GGGCCTTGGT CAGCCTCTGG    540
GTGCCAGCAG GGCAGGGGCG GAGTTCTGGG GAATGAAGGT TTTATAGGGC TCCTGGGGGA    600
GGCTCCCCAG CCCCAAGCTT                                                620
```

-continued (2) INFORMATION FOR SEQ ID NO:5:

(i) SEQUENCE CHARACTERISTICS:
(A) LENGTH: 621 base pairs
(B) TYPE: nucleic acid
(C) STRANDEDNESS: single
(D) TOPOLOGY: linear (ii) MOLECULE TYPE: protein (xi) SEQUENCE DESCRIPTION: SEQ ID NO:5:

```
TTGGATTTTG AAATGCTAGG GAACTTTGGG AGACTCATAT TTCTGGGCTA GAGGATCTGT     60

GGACCACAAG ATCTTTTTAT GATGACAGTA GCAATGTATC TGTGGAGCTG GATTCTGGGT    120

TGGGAGTGCA AGGAAAAGAA TGTACTAAAT GCCAAGACAT CTATTTCAGG AGCATGAGGA    180

ATAAAAGTTC TAGTTTCTGG TCTCAGAGTG GTGCAGGGAT CAGGGAGTCT CACAATCTCC    240

TGAGTGCTGG TGTCTTAGGG CACACTGGGT CTTGGAGTGC AAAGGATCTA GGCACGTGAG    300

GCTTTGTATG AAGAATCGGG GATCGTACCC ACCCCCTGTT TCTGTTTCAT CCTGGGCATG    360

TCTCCTCTGC CTTTGTCCCC TAGATGAAGT CTCCATGAGC TACAAGGGCC TGGTGCATCC    420

AGGGTGATCT AGTAATTGCA GAACAGCAAG TGCTAGCTCT CCCTCCCCTT CCACAGCTCT    480

GGGTGTGGGA GGGGGTTGTC CAGCCTCCAG CAGCATGGGG AGGGCCTTGG TCAGCCTCTG    540

GGTGCCAGCA GGGCAGGGGC GGAGTCCTGG GGAATGAAGG TTTTATAGGG CTCCTGGGGG    600

AGGCTCCCCA GCCCCAAGCT T                                              621
```

(2) INFORMATION FOR SEQ ID NO:6:

(i) SEQUENCE CHARACTERISTICS:
(A) LENGTH: 371 base pairs
(B) TYPE: nucleic acid
(C) STRANDEDNESS: single
(D) TOPOLOGY: linear (ii) MOLECULE TYPE: protein (xi) SEQUENCE DESCRIPTION: SEQ ID NO:6:

```
GGTGTCTTAG GCACACTGGT CTTGGAGTGC AAAGGATCTA GGCACGTGAG GCTTTGTATG     60

AAGAATCGGG GATCGTACCC ACCCCCTGTT TCTGTTTCAT CCTGGGCATG TCTCCTCTGC    120

CTTTGTCCCC TAGATGAAGT CTCCATGAGC TACAAGGGCC TGGTGCATCC AGGGTGATCT    180

AGTAATTGCA GAACAGCAAG TGCTAGCTCT CCCTCCCCTT CCACAGCTCT GGGTGTGGGA    240

GGGGGTTGTC CAGCCTCCAG CAGCATGGGG AGGGCCTTGG TCAGCCTCTG GGTGCCAGCA    300

GGGCAGGGGC GGAGTCCTGG GGAATGAAGG TTTTATAGGG CTCCTGGGGG AGGCTCCCCA    360

GCCCCAAGCT T                                                         371
```

(2) INFORMATION FOR SEQ ID NO:7:

(i) SEQUENCE CHARACTERISTICS:
(A) LENGTH: 1215 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

```
GTCGACATTG ATTATTGACT AGTTATTAAT AGTAATCAAT TACGGGGTCA TTAGTTCATA     60

GCCCATATAT GGAGTTCCGC GTTACATAAC TTACGGTAAA TGGCCCGCCT GGCTGACCGC    120

CCAACGACCC CCGCCCATTG ACGTCAATAA TGACGTATGT TCCCATAGTA ACGCCAATAG    180
```

-continued

| | | | | | | |
|---|---|---|---|---|---|---|
| GGACTTTCCA | TTGACGTCAA | TGGGTGGACT | ATTTACGGTA | AACTGCCCAC | TTGGCAGTAC | 240 |
| ATCAAGTGTA | TCATATGCCA | AGTACGCCCC | CTATTGACGT | CAATGACGGT | AAATGGCCCG | 300 |
| CCTGGCATTA | TGCCCAGTAC | ATGACCTTAT | GGGACTTTCC | TACTTGGCAG | TACATCTACG | 360 |
| TATTAGTCAT | CGCTATTACC | ATGGTGATGC | GGTTTTGGCA | GTACATCAAT | GGGCGTGGAT | 420 |
| AGCGGTTTGA | CTCACGGGGA | TTTCCAAGTC | TCCACCCCAT | TGACGTCAAT | GGGAGTTTGT | 480 |
| TTTGGCACCA | AAATCAACGG | GACTTTCCAA | AATGTCGTAA | CAACTCCGCC | CCATTGACGC | 540 |
| AAATGGGCGG | TAGGCGTGTA | CGGTGGGAGG | TCTATATAAG | CAGAGCTCTC | TGGCTAACTA | 600 |
| GAGAACCCAC | TGCTTAACTG | GCTTATCGAA | ATTAATACGA | CTCACTATAG | GGAGACCGGA | 660 |
| AGCTGATCTT | TTTATGATGA | CAGTAGCAAT | GTATCTGTGG | AGCTGGATTC | TGGGTTGGGA | 720 |
| GTGCAAGGAA | AAGAATGTAC | TAAATGCCAA | GACATCTATT | TCAGGAGCAT | GAGGAATAAA | 780 |
| AGTTCTAGTT | TCTGGTCTCA | GAGCGGTGCA | GGGATCAGGG | AGTCTCACAA | TCTCCTGAGT | 840 |
| GCTGGTGTCT | TAGGGCACAC | TGGGTCTTGG | AGTGCAAAGG | ATCTAGGCAC | GTGAGGCTTT | 900 |
| GTATGAAGAA | TCGGGGATCG | TACCCACCCC | CTGTTTCTGT | TTCATCCTGG | GCATGTCTCC | 960 |
| TCTGCCTTTG | TCCCCTAGAT | GAAGTCTCCA | TGAGCCACAG | GGCCTGGTGC | ATCCAGGGTG | 1020 |
| ATCTAGTAAT | TGCAGAACAG | CAAGTACTAG | CTCTCCCTCC | CCTTCCACAG | CTCTGGGTGT | 1080 |
| GGGAGGGGGT | TGTACAGCCT | CCAGCAGCAT | GGAGAGGGCC | TTGGTCAGCC | TCTGGGTGCC | 1140 |
| AGCAGGGCAG | GGGCGGAGTT | CTGGGGAATG | AAGGTTTTAT | AGGGCTCCTG | GGGGAGGCTC | 1200 |
| CCCAGCCCCA | AGCTT | | | | | 1215 |